US012629127B2

(12) United States Patent
Eriksson et al.

(10) Patent No.: US 12,629,127 B2
(45) Date of Patent: May 19, 2026

(54) CALIBRATION PHANTOM, METHOD, AND SYSTEM

(71) Applicant: Elekta Limited, Crawley (GB)

(72) Inventors: Markus Eriksson, Gustavsberg (SE); Joakim Sebastian da Silva, Stockholm (SE)

(73) Assignee: Elekta Limited, Crawley (GB)

( * ) Notice: Subject to any disclaimer, the term of this patent is extended or adjusted under 35 U.S.C. 154(b) by 177 days.

(21) Appl. No.: 18/565,801

(22) PCT Filed: Jun. 1, 2022

(86) PCT No.: PCT/EP2022/064885
§ 371 (c)(1),
(2) Date: Nov. 30, 2023

(87) PCT Pub. No.: WO2022/253889
PCT Pub. Date: Dec. 8, 2022

(65) Prior Publication Data
US 2024/0252138 A1 Aug. 1, 2024

(30) Foreign Application Priority Data
Jun. 1, 2021 (GB) ..................................... 2107798

(51) Int. Cl.
*A61B 6/00* (2024.01)
*A61B 6/02* (2006.01)
*A61B 6/58* (2024.01)

(52) U.S. Cl.
CPC ................ *A61B 6/584* (2013.01); *A61B 6/02* (2013.01); *A61B 6/4447* (2013.01)

(58) Field of Classification Search
None
See application file for complete search history.

(56) References Cited

U.S. PATENT DOCUMENTS

2006/0002519 A1 1/2006 Jenkins et al.
2018/0014809 A1* 1/2018 Lin ........................ A61B 6/582

FOREIGN PATENT DOCUMENTS

DE 8907424 U1 9/1989

OTHER PUBLICATIONS

"International Application Serial No. PCT/EP2022/064885, International Search Report dated Jul. 18, 2022", (Jul. 18, 2022), 3 pgs.
(Continued)

*Primary Examiner* — Hoon K Song
(74) *Attorney, Agent, or Firm* — Schwegman Lundberg & Woessner, P.A.

(57) ABSTRACT

Disclosed herein is a calibration phantom for calibrating an imaging scanner. The imaging scanner comprises a rotatable gantry, and a source of imaging radiation and a detector both configured to rotate with the gantry. The calibration phantom comprises a support structure and a plurality of boards, wherein each board comprises a planar calibration pattern formed of radiopaque material. The boards are positioned along a first axis and each board is positioned, by the support structure, at an angle with respect to each of the other boards such that each planar calibration pattern faces a different direction. The directions faced by each planar calibration pattern are substantially perpendicular to the first axis.

20 Claims, 10 Drawing Sheets

(56) References Cited

OTHER PUBLICATIONS

"International Application Serial No. PCT/EP2022/064885, Written Opinion dated Jul. 18, 2022", (Jul. 18, 2022), 7 pgs.
"United Kingdom Application Serial No. 2107798.7, Examination Report dated Feb. 24, 2022", (Feb. 24, 2022), 10 pgs.
"United Kingdom Application Serial No. 2107798.7, Examination Report dated Dec. 7, 2023", (Dec. 7, 2023), 3 pgs.

* cited by examiner

526

514

522

512

500

524

518

516

514

512

522

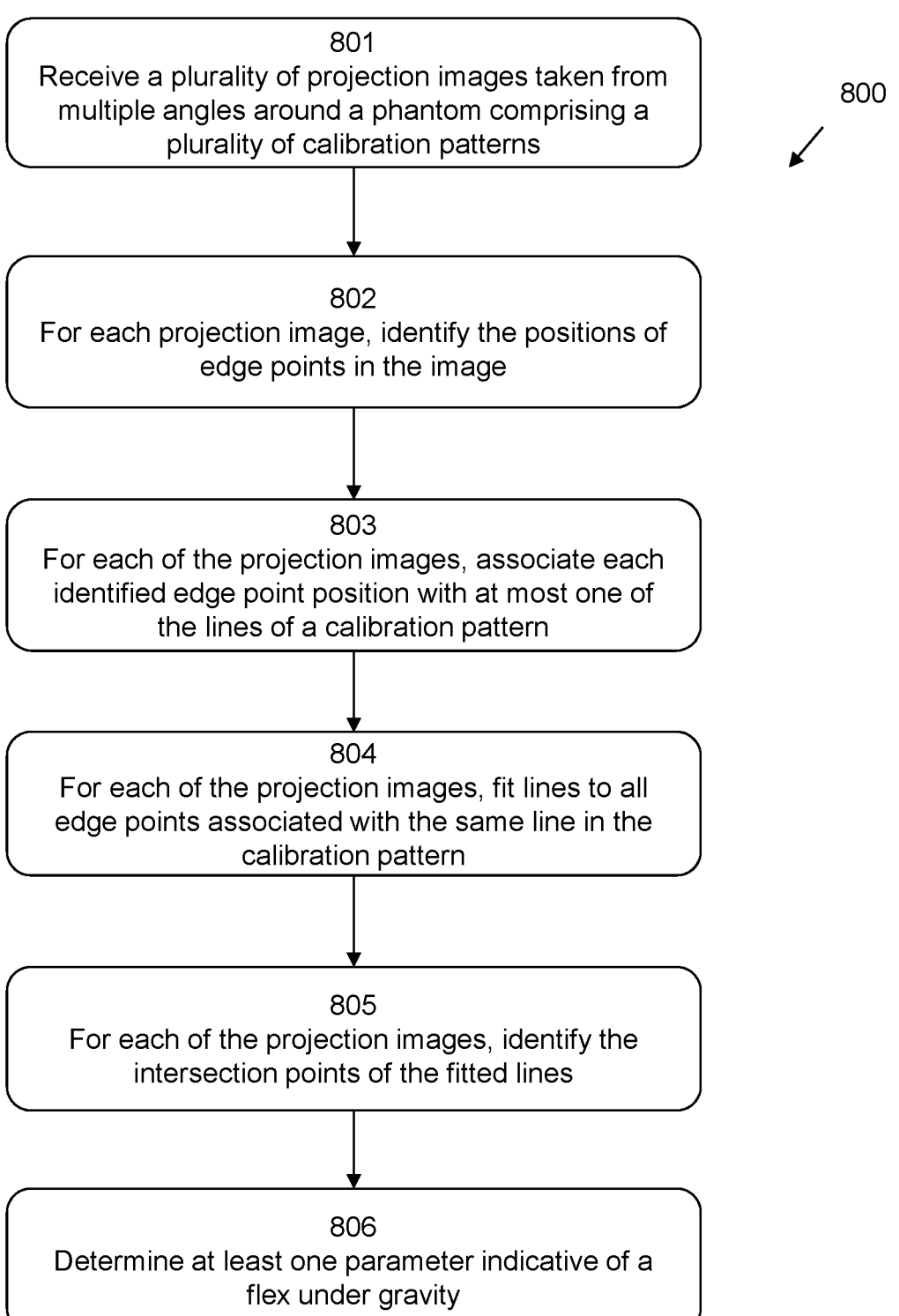

801
Receive a plurality of projection images taken from multiple angles around a phantom comprising a plurality of calibration patterns

800

802
For each projection image, identify the positions of edge points in the image

803
For each of the projection images, associate each identified edge point position with at most one of the lines of a calibration pattern

804
For each of the projection images, fit lines to all edge points associated with the same line in the calibration pattern

805
For each of the projection images, identify the intersection points of the fitted lines

806
Determine at least one parameter indicative of a flex under gravity

Fig. 8

CALIBRATION PHANTOM, METHOD, AND SYSTEM

PRIORITY APPLICATIONS

This application is a U.S. National Stage Filing under 35 U.S.C. § 371 from International Application No. PCT/EP2022/064885, filed on Jun. 1, 2022, and published as WO2022/253889 on Dec. 8, 2022, which claims the benefit of priority to British Application No. 2107798.7, filed on Jun. 1, 2021; the benefit of priority of each of which is hereby claimed herein, and which applications and publication are hereby incorporated herein by reference in their entireties.

This disclosure relates to a calibration phantom and associated systems and methods for calibrating an imaging scanner.

BACKGROUND

Radiotherapy devices typically comprise imaging capabilities provided by an imaging system configured to provide images of the patient. These images assist with treatment planning and positioning of the patient. The imaging system may for example comprise a source of kilovolt (kV) energy radiation, such as X-rays, and a detector such as a flat panel detector. Such an imaging system is typically mounted on the rotatable gantry of the radiotherapy device at an angle relative to a treatment apparatus. An example imaging modality which may be incorporated into a radiotherapy device is cone beam computed tomography (or CBCT). CBCT images are used in the field of radiotherapy to determine, pre-treatment, how accurately a patient is positioned on a treatment surface in comparison with the images which formed the basis of the patient's treatment plan.

CBCT is an imaging modality involving the use of a source of imaging radiation, such as X-rays. The imaging radiation is emitted in a cone shape. These divergent beams of imaging radiation pass through the patient, are detected by the detector, and a projection image is acquired. It is possible to generate a three-dimensional image of an imaging subject from multiple such projection images acquired at different angles around the imaging subject.

In a completely rigid, mathematically ideal system, the relative distance between each component of the imaging apparatus would be fixed and stable, and the relative orientations of these components would not change. However, in practice, the relative distances and orientations of the components of the imaging apparatus are not fixed and stable. As the imaging system is rotated by the gantry, the imaging system, gantry, and the mechanical means via which the imaging system is coupled to the gantry undergo small mechanical shifting or 'flexing' as a function of gantry angle. In an implementation in which the imaging system forms part of a radiotherapy apparatus, the flexing of the gantry and imaging system components under gravity is compounded by the heavy treatment apparatus. This treatment apparatus may comprise a heavy source of therapeutic radiation, and for example may take the form of a linear accelerator. This heavy treatment apparatus causes additional flexing of the gantry as a function of rotation angle which affects the relative positions of the components of the imaging system.

To account for this flexing and ensure good image reconstruction quality, the position of the kV source and detector must be accurately and precisely known as a function of gantry rotation angle. This can be achieved by taking images of a phantom with known features at various gantry rotation angles, and using the resulting projection images to compute information about the position and/or orientation of the kV source and detector as a function of gantry angle. FIG. 2 depicts a phantom 300 in accordance with the prior art which has been used in such calibration methods to date.

Phantom 300 comprises a set of radio-opaque ball bearings 330 aligned in a specific pattern, which includes an upper ring 310 of ball bearings spaced around a circumference of the phantom and a lower ring 320 of ball bearings spaced around the circumference of the phantom. The phantom 300 is functional, however there are several drawbacks to calibrating an imaging apparatus using such a phantom 300. For example, the positions of the ball bearings 330 must be aligned to the pattern with very high precision, making manufacturing of the phantom 300 complex and expensive. Even a small misalignment in ball-bearing 330 position will result in suboptimal calibration. Further, in the projected image of the ball bearings 330, each of the ball bearings takes up a small number of pixels, with the subpixel position of the ball-bearing being determined based on the smaller number pixels at the edge of the ball-bearing in the projection image. The small number of pixels per ball-bearing adds an extra uncertainty in the method to determine the sub-pixel position of the ball-bearing centre.

Also, some modern CBCT systems allow the detector to be shifted to an offset 'half-fan' position in order to increase the field-of-view of the imaged object. When imaging in a half-fan mode, it is possible that the projection images will not capture the entire phantom 300 if it is placed centrally in the field of view of the imaging system. However, the robustness of calibration methods using phantom 300 suffer when only part of phantom 300 is visible in every projection image. Therefore, an alternative to phantom 300 is desirable in order to ensure the required accuracy of calibration for imaging modes with a shifted detector. In addition, if the entire phantom is not included in the projection images for each gantry angle, different bearing balls 300 may be observed in different projection images when scanning in a half-fan mode, increasing the sensitivity to small deviations in relative ball bearing positions.

The present invention seeks to address these and other disadvantages encountered in the prior art.

SUMMARY

An invention is set out in the claims.

According to an aspect, there is provided a calibration phantom for calibrating an imaging scanner. The imaging scanner comprises a rotatable gantry, and a source of imaging radiation and a detector both configured to rotate with the gantry. The calibration phantom comprises a support structure and a plurality of boards, wherein each board comprises a planar calibration pattern formed of radiopaque material, wherein the boards are positioned along a first axis. Each board is positioned, by the support structure, at an angle to each of the other boards such that each planar calibration pattern faces a different direction, wherein the directions faced by each planar calibration pattern are substantially perpendicular to the first axis.

Optionally, the source of imaging radiation and detector are configured to rotate with the gantry by virtue of being coupled to the gantry.

Optionally, the plurality of boards comprises at least three boards, with each board being positioned, by the support structure, at an oblique angle with respect to the other boards such that each planar calibration pattern faces a different direction.

Optionally, each board is positioned, by the support structure, such that when the calibration phantom is imaged via imaging radiation incident from any direction perpendicular to the first axis, at least a portion of at least two planar calibration patterns are included in the image.

Optionally, the plurality of boards comprises at least a first board comprising a first planar calibration pattern, a second board comprising a second planar pattern, and a third board comprising a third planar pattern. The first planar pattern is positioned, by the support structure, to face in a first direction, the second planar pattern is positioned, by the support structure, to face in a second direction, and the third planar pattern is positioned, by the support structure, to face in a third direction. The first, second and third directions all meet at oblique angles with respect to one another.

Optionally, the boards of the plurality of boards are separated from one another along the first axis.

Optionally, each of the plurality of boards comprises a substrate, and the planar calibration pattern is formed of metal layered on the substrate. Each of the calibration patterns may be formed via a subtractive manufacturing process. The subtractive manufacturing process may comprise one or more of the following processes: chemical etching, physical milling, digital lithography, photolithography.

Optionally, the support structure has a central axis aligned with or parallel to the first axis.

Optionally, the support structure is comprised of a plurality of stackable elements each stacked along the first axis, each stackable element comprising at least one recess configured to hold one of the plurality of boards in position.

Optionally, the planar calibration patterns each comprise a plurality of intersecting lines. The planar calibration patterns may be checkerboard patterns comprising a repeating pattern of diamonds.

Disclosed herein is a calibration phantom for calibrating an imaging scanner. The imaging scanner comprises a rotatable gantry, and a source of imaging radiation and a detector both configured to rotate with the gantry. The calibration phantom comprises a support structure and a plurality of boards, wherein each board comprises a planar calibration pattern formed of radiopaque material, wherein the boards are stacked with respect to one another along a stacking axis. Each board is positioned, by the support structure, at an angle to each of the other boards such that each planar calibration pattern faces a different direction, wherein the directions faced by each planar calibration pattern are substantially perpendicular to the stacking axis.

According to an aspect, there is provided a method of calibrating an imaging scanner, the imaging scanner comprising a rotatable gantry, and a source of imaging radiation and a detector both configured to rotate with the gantry. The method comprising receiving a plurality of projection images, taken from multiple gantry rotation angles, of a phantom positioned within a field of view of the imaging scanner. The phantom comprises a plurality of boards each comprising a calibration pattern formed of radiopaque material, and each board is positioned, by a support structure, at an oblique angle to each of the other boards such that each planar calibration pattern faces a different direction. The method further comprises determining, based on the projection images, at least one calibration parameter. The at least one calibration parameter is indicative of a difference between a nominal position or orientation of a component of the imaging scanner compared to a true position or orientation of the component of the imaging scanner.

The at least one calibration parameter may be indicative of a flex under gravity of the source of imaging radiation or detector. For example, the difference between the nominal position or orientation of the component and the true position or orientation of the component may be indicative of flexing under gravity of the component.

Optionally, the method further comprises acquiring the projection images by taking multiple projection images at the multiple gantry rotation angles. The method further comprises identifying the positions of edge points in each projection image, and associating the identified edge point positions with lines of the calibration pattern.

Optionally, the calibration pattern further comprises a plurality of intersecting lines, where the lines intersect to form intersection points, and the method further comprises identifying intersection points in the projection images and determining the at least one calibration parameter based on the identified intersection points in each projection image.

According to another aspect, there is provided a system for calibrating an imaging scanner, the imaging scanner comprising a rotatable gantry, and a source of imaging radiation and a detector both configured to rotate with the gantry. The system comprises a phantom comprising a plurality of boards, each board of the plurality of boards comprising a calibration pattern formed of radiopaque material, and each board positioned, by a support structure, at an oblique angle to each of the other boards such that each planar calibration pattern faces a different direction. The system further comprises a computer-readable medium comprising computer-executable instructions which, when executed by a processor, cause the processor to receive projection images of the phantom taken by the imaging scanner from multiple gantry rotation angles and, based on the projection images, determine at least one calibration parameter. The at least one calibration parameter is indicative of a difference between a nominal position or orientation of a component of the imaging scanner compared to a true position or orientation of the component of the imaging scanner.

The at least one calibration parameter may be indicative of a flex under gravity of the source of imaging radiation or detector. For example, the difference between the nominal position or orientation of the component and the true position or orientation of the component may be indicative of flexing under gravity of the component.

Optionally, the phantom is the phantom as described above or elsewhere herein.

Optionally, the at least one calibration parameter relates to at least one of a position of the source of imaging radiation, the position of the detector, and the orientation of the detector.

Optionally, the at least one calibration parameter is determined as a function of gantry rotation angle.

According to an aspect, a computer readable medium is provided which comprises computer-executable instructions which, when executed by a processor, cause the processor to perform the method described above or elsewhere herein.

Disclosed herein is a method of calibrating an imaging scanner. The imaging scanner comprises a rotatable gantry, and a source of imaging radiation and a detector both configured to rotate with the gantry. The method comprises positioning a phantom comprising a plurality of boards within a field of view of the imaging scanner, each board of the plurality of boards comprising a calibration pattern formed of radiopaque material, and each board is positioned, by a support structure, at an oblique angle to each of the other boards such that each planar calibration pattern faces a different direction. The method comprises acquiring projection images of the phantom from multiple gantry rotation angles, and determining, based on the projection images, at least one calibration parameter indicative of a flex under gravity of the source of imaging radiation or detector.

FIGURES

Specific embodiments are now described, by way of example only, with reference to the drawings, in which:

FIG. 8 depicts a method according to the present disclosure;

DETAILED DESCRIPTION

Figure 1:
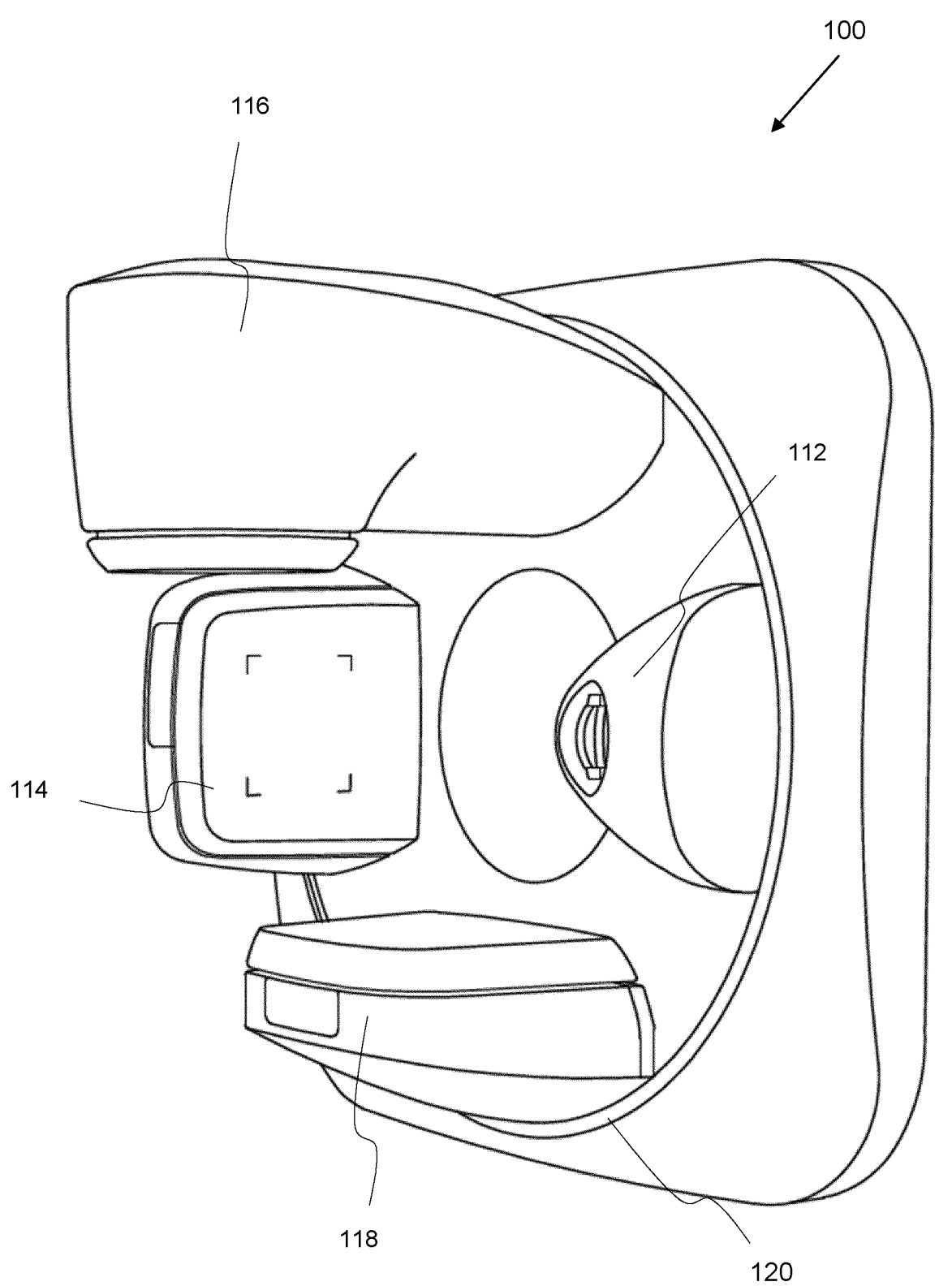
FIG. 1 depicts a radiotherapy device or apparatus according to the present disclosure.

In overview, the present disclosure relates to a calibration phantom for calibrating an imaging scanner. The imaging scanner may be a CBCT scanner, and may form part of a radiotherapy apparatus. The imaging scanner comprises a rotatable gantry. The imaging scanner comprises a source of imaging radiation and a detector both configured to rotate with the gantry. The source of imaging radiation and detector may thus be rotated to different angles around a patient to acquire projection images at multiple angles around the patient. These images may be formed into a 3D image via a reconstruction algorithm.

The calibration phantom itself comprises a support structure and a plurality of boards. Each board comprises a planar calibration pattern formed of radiopaque material, and thus the patterns can be seen in the projection images acquired by the imaging scanner. The boards are positioned with respect to one another along a first axis. This first axis may be the central axis of the support structure. Each board is positioned, by the support structure, at an angle to each of the other boards such that each planar calibration pattern faces a different direction, wherein the directions faced by each planar calibration pattern are substantially perpendicular to the first axis. This has the technical effect of ensuring that, when the phantom is placed in the imaging scanner with the first axis parallel with the gantry rotation axis, at least a portion of a calibration pattern is visible in the projection images, regardless of gantry rotation angle. In a particularly advantageous implementation, there are at least three boards, and each is positioned at an oblique angle to the other boards. This arrangement ensures that calibration patterns from at least two different boards are visible in each projection, and the same boards are visible in each pair of projections separated by a 180° gantry rotation.

The disclosure also relates to a system for calibrating an imaging scanner, comprising the phantom and a computer-readable medium comprising computer-executable instructions which, when executed by a processor, cause the processor to acquire (or otherwise receive) projection images of the phantom from multiple gantry rotation angles, and determine, based on the projection images, at least one parameter relating to a sag under gravity of the source of imaging radiation or detector. The system may also comprise the scanner itself.

Methods of the present disclosure seek to calibrate nine parameters for an imaging scanner which has components subject to sag and flexing under gravity: the position $(x\_s, y\_s, z\_s)$ of the source of imaging radiation and the position $(x\_d, y\_d, z\_d)$ and orientation/rotation $(xr\_d, yr\_d, zr\_d)$ of the detector. Due to the flex in the mechanical system while rotating the gantry, these parameters vary as a function of the gantry angle, and the present calibration method finds the flex parameters as a function of the gantry angle.

Some prior methods for calibrating optical cameras have made use of checkerboard patterns. In such calibration tasks, it is usually desired to determine between three and five intrinsic camera parameters and six extrinsic parameters. However, these prior methods and calibration phantoms, which make use of a single checkerboard visible to an optical camera, are not appropriate for use with imaging scanners in which the flex or sag under gravity is an issue, such as for a CBCT system. That is because these prior methods rely on the intrinsic camera parameters being constant between different pictures. That is not the case for a CBCT scanner, in which the flex and sag causes the relative position and orientation between the imaging components to vary as a function of gantry rotation angle. The present phantom overcomes this problem via a particular positioning of calibration patterns—along an axis and each facing a different direction in the manner described below. This means that at least a portion of two planar calibration patterns will be visible in each projection image, which allows the determination of all nine calibration parameters. Also, the present calibration methods do not depend on the relative positions of the boards/patterns, because the relative position information is determined as part of the calibration.

Manufacturing techniques for electronic circuit boards, for example etching and lithography, may be used to produce the boards comprising the radiopaque calibration patterns. Accordingly, the boards may comprise a substrate with a metal coating, such as a copper coating, which has undergone a subtractive manufacturing process to produce a suitable calibration pattern. Such PCB techniques are highly accurate processes in which planar (2D) patterns can be made to an accuracy of micrometres at a low cost. Copper, the material most commonly used in circuit boards, has the benefit of being radioopaque. Patterns on circuit boards will therefore be highly visible in x-ray imaging.

Geometric calibration for optical cameras is a different and somewhat simpler problem than geometric calibration for an imaging scanner which may undergo flexing under gravity. This sagging/flexing is not a problem for optical camera calibration and there are thus fewer parameters to determine. For example, in the case of an optical camera, there are fewer parameters that change from projection image to projection image. The present checkerboards define lines which can be identified and parametrized with high accuracy and precision. Their numerous intersection points on the image board, i.e. imaged corners of the checkerboard squares that corresponds to points in the 3D checkerboard object, are then used to calculate the nine desired system parameters.

In an implementation of the presently disclosed phantom, the phantom may therefore comprise circuit boards with checkerboard patterns, or other well-defined patterns of intersecting lines, and a calibration method may involve taking x-ray images from multiple gantry rotation angles. The x-ray images of the boards are used to define projected points, which in turn are used to determine the x-ray source and detector geometric parameters for each gantry angle. The method uses information from several or all images taking at different gantry angles during the calibration to determine the relative positions and rotations of the circuit boards. Hence, the calibration result does not depend on the accuracy or precision of the phantom assembly, but relies instead on the accuracy and precision of the pattern fabrication (which is high) and the flatness of the circuit boards, which is ensured by the rigidity of the boards and the support structure.

FIG. 1 depicts a radiotherapy device 100 suitable for delivering, and configured to deliver, a beam of radiation to a patient during radiotherapy treatment. The device 100 and its constituent components will be described generally for the purpose of providing useful accompanying information to aid the understanding of the presently disclosed calibration phantom(s) and method(s). The device 100 depicted in FIG. 1 is in accordance with the present disclosure and is suitable for use with the disclosed calibration phantom(s) and calibration method(s).

Radiotherapy can be described as the use of ionising radiation, such as high energy X-rays, to treat a human or animal body. Radiotherapy is commonly used to treat tumours within the body of a patient or subject. In such treatments, ionising radiation is used to irradiate, and thus destroy or damage, cells which form part of the tumour.

The device 100 depicted in FIG. 1 comprises a source of therapeutic radiation 116 and a radiation detector 118. The radiation source 116 may comprise a beam generation system. For a linac, the beam generation system may comprise a source of RF energy, an electron gun, and a waveguide. The source of therapeutic radiation 116 is attached to the rotatable gantry 120 so as to rotate with the gantry 120. In this way, the radiation source 116 is rotatable around the patient so that a treatment beam can be applied from different angles around the gantry 120.

The radiation detector 118 is positioned opposite to the radiation source 116. The radiation detector 118 is suitable for producing, and configured to produce, radiation intensity data. In particular, the radiation detector 118 is positioned and configured to detect the intensity of therapeutic radiation which has passed through the patient. The radiation detector 118 may also be described as radiation detecting means, and may form part of a portal imaging system.

The device 100 depicted in FIG. 1 also comprises an imaging system comprising components configured to rotate with a gantry 120. Such components include both a source of imaging radiation 112 and a detector 114 which are affixed to the gantry 120. The source of imaging radiation 112 may be a source of kV X-rays. Together with other components such as connecting wires, on-board processors and the like, the source of imaging radiation 112 and imaging detector 114 comprise an imaging apparatus or imaging system which is rotatable around a patient. The imaging system provides the device 100 with imaging capabilities, and in particular X-ray, CBCT and/or CT imaging capabilities. By rotating the imaging system around a patient, projection images can be acquired from multiple gantry angles, and a three-dimensional image can be reconstructed based on these projection images using known tomographical techniques. The imaging capabilities of the device 100 mean that the device 100 is an imaging scanner.

The source of imaging radiation 112 and imaging detector 114 are coupled to the gantry 120. The components 112 and 114 are heavy and there is a flexing or 'sagging' effect as gravity acts on these components as the gantry 120 rotates. Unless this flexing is taken into account, the reconstructed images acquired by the imaging scanner may be suboptimal. These flexing effects are further exacerbated where the imaging scanner is also a radiotherapy device comprising a detector 118 and a heavy treatment head containing a radiation source 116.

The device 100 further comprises a controller (not shown) in the form of a computer, processor, or other processing apparatus. The controller may be formed by several discrete processors; for example, the controller may comprise a imaging processor, which controls the imaging components such as the source of imaging radiation 112, while being configured to receive data and images acquired by the imaging detector 114; an RT apparatus processor, which controls the operation of the RT components such as the source of therapeutic radiation 116 while being configured to receive data and images acquired by the detector 118; and a patient support surface processor which controls the operation and actuation of a patient support surface (not shown). The controller is communicatively coupled to a memory, e.g. a computer readable medium. The controller may be in the form depicted in FIG. 10 and described below.

The device 100 also comprises several other components and systems as will be understood by the skilled person. For example, in order to ensure the linac does not leak radiation, appropriate shielding is also provided. In use, the device 100 will form part of a radiotherapy system which further comprises a patient positioning system which may be used to position a patient in order for the patient to be imaged and/or treated. Such a patient positioning system may also be used to position a phantom within a field of view of the device 100 for the purposes of performing QA and calibration methods.

Figures 2A, 2B:
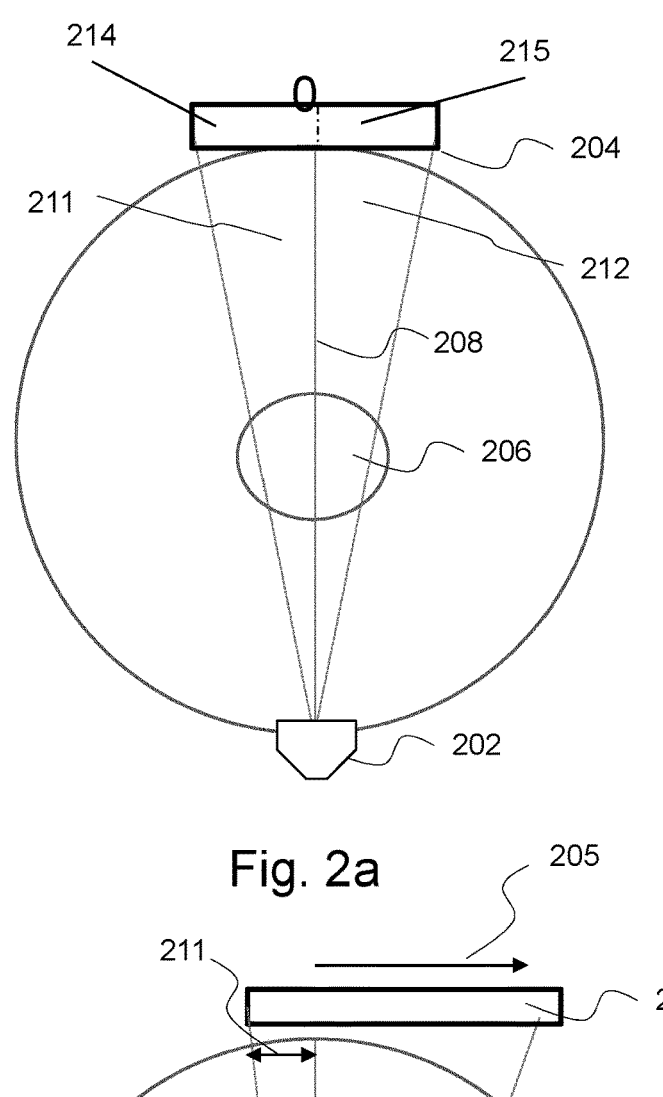
FIG. 2a is a schematic diagram depicting a configuration suitable for 'full-fan' operation.
FIG. 2b is a schematic diagram depicting a configuration suitable for 'half-fan' operation.

In some imaging scanners, the field of view can be adjusted. This functionality is depicted in FIGS. 2a and 2b. As shown in FIGS. 2a and 2b, the X-ray source 202 of a CBCT imaging scanner (which may also be a radiotherapy device) is configured to emit a fan-shaped beam. The fan-shaped beam is shown in FIGS. 2a and 2b by the dashed lines, and the central axis 208 of the beam is shown as a solid line. The size of the fan-shape beam can be altered depending on the size of the patient and/or the region to be imaged.

FIG. 2a is a schematic diagram depicting a configuration suitable for 'full-fan' operation, while FIG. 2b is a schematic diagram depicting a configuration suitable for 'half-fan' operation. As shown in FIG. 2a, for full-fan operation, the panel detector 204 is centred on the central axis 208 of the X-ray beam, i.e. the central axis 208 of the 'fan' formed by the radiation. The panel detector 204 may be described as being located in a first position, first orientation or a first location suitable for full-fan scanning.

In the 'full-fan' configuration, the panel detector 204 and X-ray source 202 may be rotated 180 degrees around the patient in order to achieve projection data. When the panel detector 204 and X-ray source 202 are rotated by 180 degrees, plus the fan angle, a full image of the target location can be produced using imaging software and known reconstruction techniques.

As shown in FIG. 2b, for 'half-fan' operation, the detector panel 204 is positioned such that it is not centred on the central axis 208 of the X-ray fan. Instead, the panel detector 204 is moved laterally to the side. In other words, the panel detector 204 is shifted laterally, or sideways, with respect to its position during full-fan operation. The panel detector 204 may also be referred to as an 'off-centre' panel detector 204. The panel detector 214 may be described as being located in a second position, a second orientation or a second location suitable for half-fan scanning.

Figure 3:
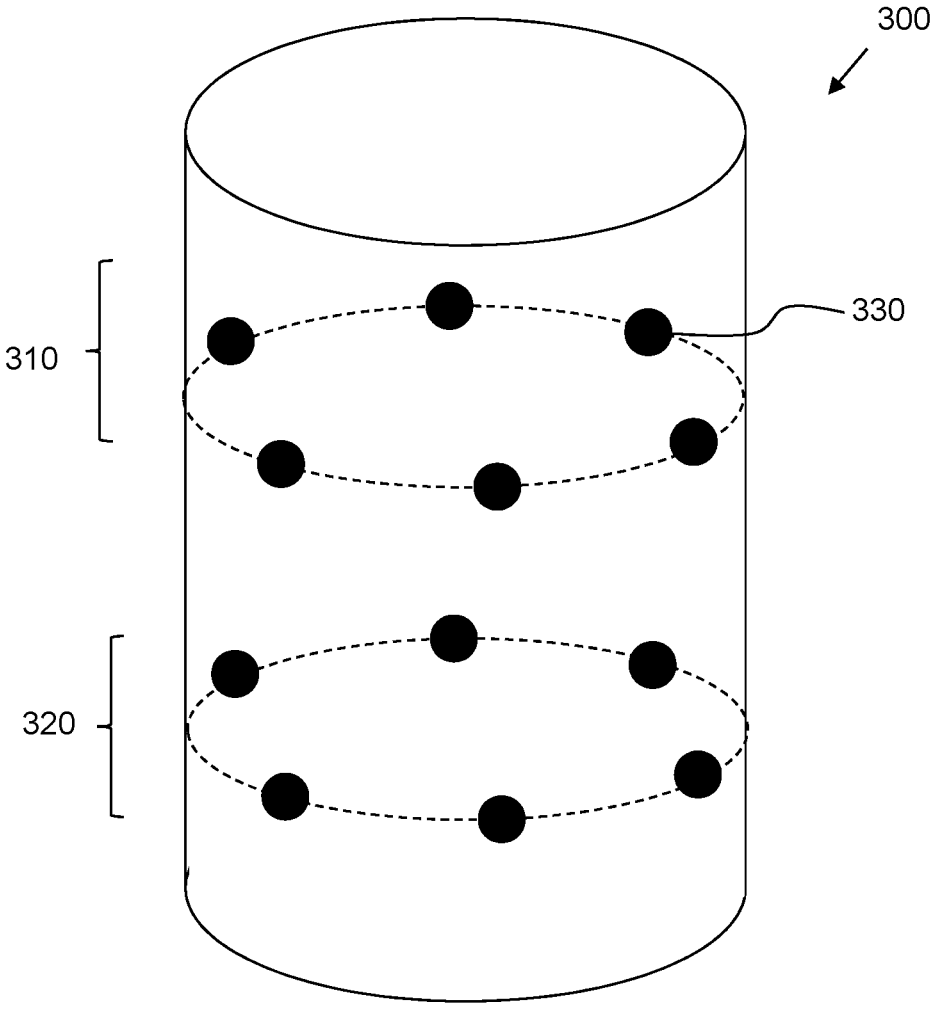
FIG. 3 depicts a phantom comprising ball-bearing in accordance with the prior art.

Prior methods of calibrating systems for both full and half fan operation benefitted from having the entire phantom, such as the phantom depicted in FIG. 3, to be shown in every projection angle to ensure that the resulting projection images contain enough points to perform the calibration. However, this is problematic for half-fan imaging because only half of the phantom will be imaged at each angle. When imaging these prior phantoms in a half-fan scanning mode, then only roughly half the ball-bearings will be visible in the resulting projection images. Calibration methods which rely on fitting geometric shapes (e.g. ellipses) based on the known arrangement of the ball-bearings will not provide an accurate calibration when half the ball-bearings cannot be found in the image. Also, opposing projection images, i.e. projection images which are taken from gantry positions separated by roughly or exactly 180°, may not depict the same bearing balls. This puts higher demand on knowing the exact phantom geometry, e.g. though accurate manufacturing of the phantom. The geometry parameters (e.g. which describe the flex and sag of the system with gravity) may therefore not be determined to desired accuracy for the half fan/offset imaging mode when calibrating using these known phantoms.

The phantom of the present application mitigates and/or addresses these issues by using a phantom which comprises a planar calibration pattern which comprises intersecting lines of radiopaque material. At least some of the lines which make up the pattern of intersecting lines have a component of extension along the width and length of the pattern. By providing radiopaque lines which have a degree of extension across the width and length of the calibration pattern, the projection images from a half-fan scan are likely to comprise pairs of opposing projection images in which different parts of the same line of the calibration pattern can be seen. This allows opposing projection images to be more easily matched up and aligned with respect to one another in a way which is not possible when using a pattern comprising ball-bearings. By identifying when different parts of the same line(s) have been imaged in this way, calibration methods are able to provide a robust calibration even when the entire phantom is not visible in every projection image. An example of a suitable calibration pattern is a diamond checkerboard pattern.

Figure 4A:
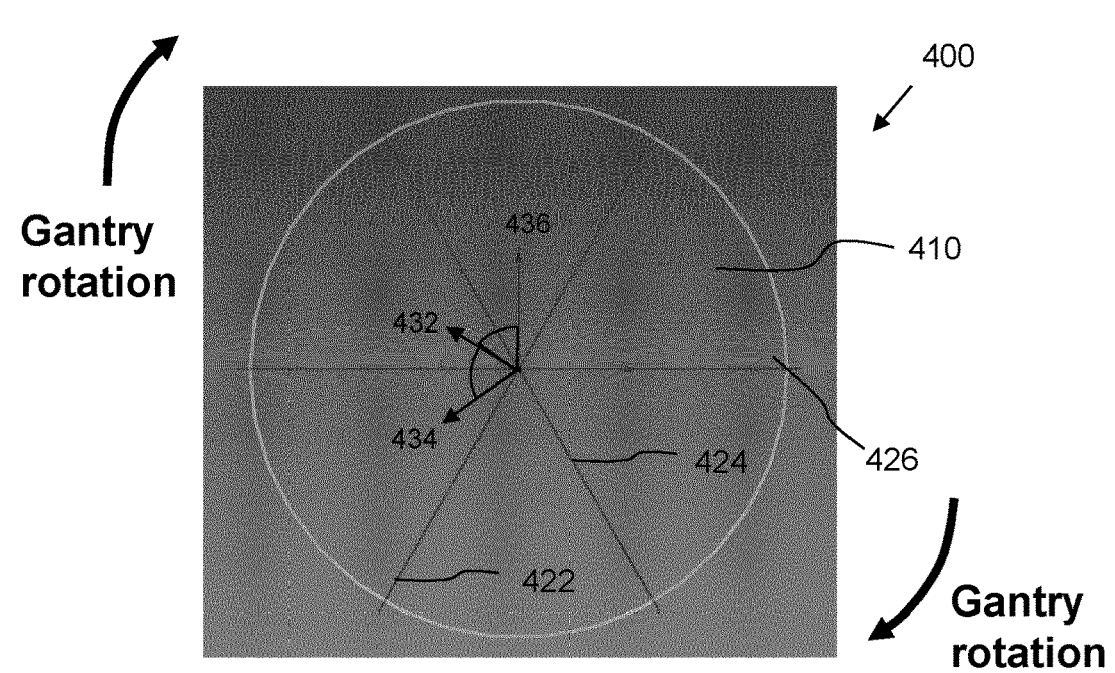
FIGS. 4a and 4b depict a phantom according to the present disclosure, in which a support structure of the phantom is depicted as transparent to aid understanding.
Figure 4B:
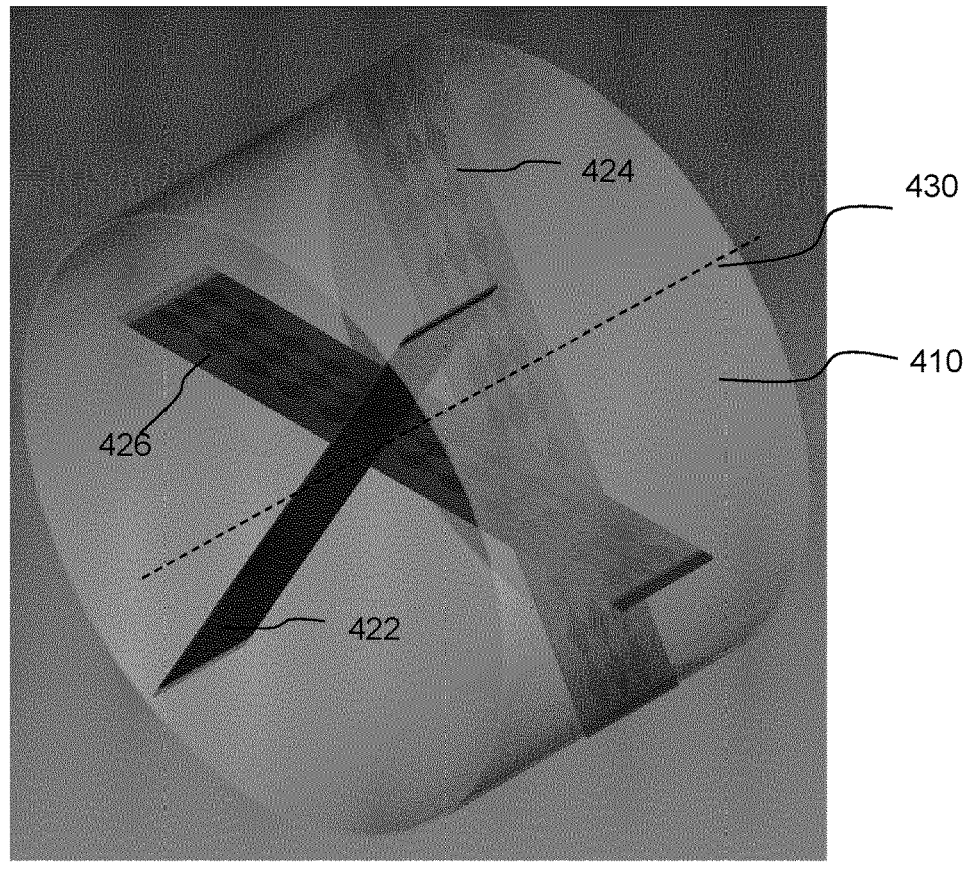

FIGS. 4a and 4b depict a phantom 400 according to the present disclosure. The phantom comprises a support structure 410 and a plurality of boards 422, 424, 426. The support structure 410 is comprised of a radiolucent material, or at least a material which is more radiolucent than the calibration patterns, and is configured to hold/support the boards 422, 424, 426 in an arrangement such that each board faces a different direction. The support structure 410 further holds/supports the boards 422, 424, 426 such that they are positioned with respect to one another along a first axis 430. The boards are positioned this way such that, when the phantom 400 is imaged from a direction perpendicular to the first axis 430, the overlap of the calibration patterns when projected onto the detector is minimised.

Figure 6:
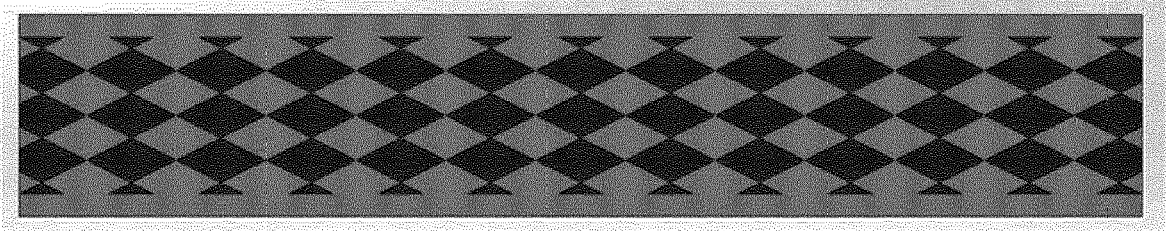
FIG. 6 depicts a calibration pattern according to the present disclosure.

The boards 422, 424, 426 are planar and elongated, and have rectangular faces. Each board 422, 424, 426 comprises a calibration pattern. The calibration patterns are formed of radiopaque material. The radiopaque patterns shown in FIGS. 4a, 4b are checkerboard patterns. The checkerboard patterns shown comprise repeating diamond shapes. The pattern is depicted in FIG. 6 and is described in more detail below. The radiopaque pattern extends along substantially the entire face of one of the main rectangular faces of the boards. The use of a checkerboard pattern is advantageous compared to the ball-bearings employed in the prior art phantom 300 depicted in FIG. 3, because the checkerboard pattern defines both lines and points. Parts of the same line will be visible for all gantry angles regardless of whether the imaging scanner is in a full or a half fan scanning mode. Not all lines need to be visible in this method. The accuracy to determine the position of a line in a calibration pattern is also greater than for determining a ball bearing position, because in the majority of cases the lines will be comprised of more pixels in the projection images.

The support structure 410 is cylindrical and has a diameter of similar length to the length of each board 422, 424, 426. The calibration patterns depicted span the length of each board, and each board spans the diameter of the cylindrical support structure.

The support structure 410 supports and positions the boards 422, 424, 426 such that they are positioned with respect to one another along the first axis 430. When viewing FIG. 4a, the first axis 430 is into the plane of the page. The first axis 430 aligns with the central axis of the cylindrical support structure 410. The boards 422, 424, 426 are positioned such that the centres of each board are spaced apart in a direction parallel with the first axis 430. The support structure 410 positions the boards 424, 426, 428 at an oblique angle to one another such that each planar calibration pattern faces a different direction. The oblique angle(s) ensure the boards are not coplanar (in which case the angle would be zero) or perpendicular to one another (in which case the angle would be) 90°. The boards 424, 426, 428 are therefore positioned/stacked/supported in a non-coplanar arrangement.

Each planar calibration pattern comprises a central length axis and a central width axis. The boards 424, 426, 428 are positioned/stacked along the first axis 430 such that the central width axes of the boards align with one another, parallel to a central axis 430 of the support structure 410. Each board 424, 426, 428 is translated along the central axis 430 and rotated around the central axis 430 compared to the previous board. The first axis 430 may be referred to as a 'stacking axis' herein, along which the boards 424, 426, 428 may be stacked with respect to one another.

In the example shown in FIGS. 4a and 4b, the first board 422 comprises a first calibration pattern which faces a first direction 432; the second board 424 comprises a second calibration pattern which faces a second direction 434; and the third board 426 comprises a third calibration pattern which faces a third direction 436. Each of the first, second and third directions 432, 434, 436 meet at an oblique angle with respect to one another. In the implementation depicted in FIGS. 4a-4b, the boards 424, 426, 428 are positioned at or around 60 degrees with respect to one another. Each of the first, second and third directions 432, 434, 436 faced by the planar calibration patterns is substantially perpendicular to the first axis.

In use, the calibration phantom 400 is placed with the first axis (or, equivalently for the implementation depicted in the figures, its central axis) roughly aligned with the gantry rotation axis. This positioning with respect to the rotatable gantry of an imaging scanner is depicted by curved arrows in FIG. 4a. Each of the directions 432, 434, 436 faced by a calibration pattern is an example direction from which imaging direction may be directed at the phantom 400.

During a calibration process, projection images of the phantom are taken from multiple gantry rotation angles and, based on the projection images, parameter(s) are obtained which are indicative of the flexing under gravity of the components of the imaging scanner. The use of planar calibration patterns allows the calibration to be more accurate compared to prior calibration methods. The use of checkerboard patterns in particular is advantageous, because they provide a large number of points defined by the corners of the squares, rectangles, or diamonds. The calibration can then rely on the fact that straight lines formed by the squares, rectangles, or diamonds remain straight after projective transformation.

Further, by positioning (stacking) the boards with respect to one another such that each planar calibration pattern faces a different direction, with these directions substantially perpendicular to the first (stacking) axis, it is ensured that at least a portion of a pattern can be viewed from every gantry rotation angle. Further, because of the manner in which the boards are positioned, there can be no confusion regarding which board the patterns in the projection images are associated with. In the implementation shown in FIGS. 4a-4b, in which at least three boards are used and the boards are each positioned at an oblique angle with respect to one another, a portion of at least two different boards will be found in all projection images, regardless of gantry rotation angle.

As described above, the prior phantom 300 depicted in FIG. 3 must have ball bearings aligned to a pattern with very high precision to ensure high accuracy, making manufacturing of the phantom complex and expensive. In contrast, the only accuracy needed for the present phantom is in the 2D board pattern It is significantly easier to ensure high accuracy for a planar calibration pattern; for example, high accuracy is an intrinsic property in circuit board manufacturing. PCB manufacturing gives a high accuracy at a low manufacturing cost.

The relative positioning of the patterns 310 and 320 must also be highly exact, or known to a high degree of accuracy and precision, to ensure accurate results when using prior phantom 300. However, using the presently disclosed calibration patterns, particularly a pattern with intersecting lines such as a checkerboard, the exact position of the boards themselves, relative to the other boards or to the system geometry, can be easily determined as part of the calibration process, making the phantom 400 easy to manufacture compared to known phantoms. This is because the pattern on a single board allows eight degrees of freedom to be determined, whereas the position of a board relative to another board can be fully characterised by six degrees of freedom (three translational and three rotational). Hence, a projection image showing two boards can be used to determine up to 16 parameters, whereas the configuration itself has 15 degrees of freedom (nine projection parameters and six relative translation and rotations of the second board relative to the first). In the case of three boards visible in a projection image, there are 21 degrees of freedom which characterise the configuration, but the images provide the ability to determine 24 parameters. Thus, regardless of the number of projection images, it is possible to fully determine both the projection parameters and phantom geometry in the same optimisation process.

Another way of discussing the above-described advantageous nature of the present phantom and method is to discuss the ground truth used by the calibration methods. For the present phantom, the checkerboard patterns themselves act as the ground truth. It is possible to determine the relative positioning of the patterns with respect to one another. It is possible to perform the calibration process to determine the calibration parameters as part of the same process. In contrast, for a prior ball-bearing phantom, it is necessary for either high accuracy on the known positioning of the ball bearings with respect to one another to provide the ground truth, or the ball-bearing geometry must be determined as part of the optimisation method. But, to perform a determination of the ball-bearing geometry as part of the optimisation, many images of the ball-bearings from a highly stable or pre-calibrated imaging geometry must be provided in order to provide sufficient accuracy for the determination because a single projection image of the ball-bearings does not provide as many degrees of freedom as an image of a calibration pattern according to the present disclosure.

Figure 5A:
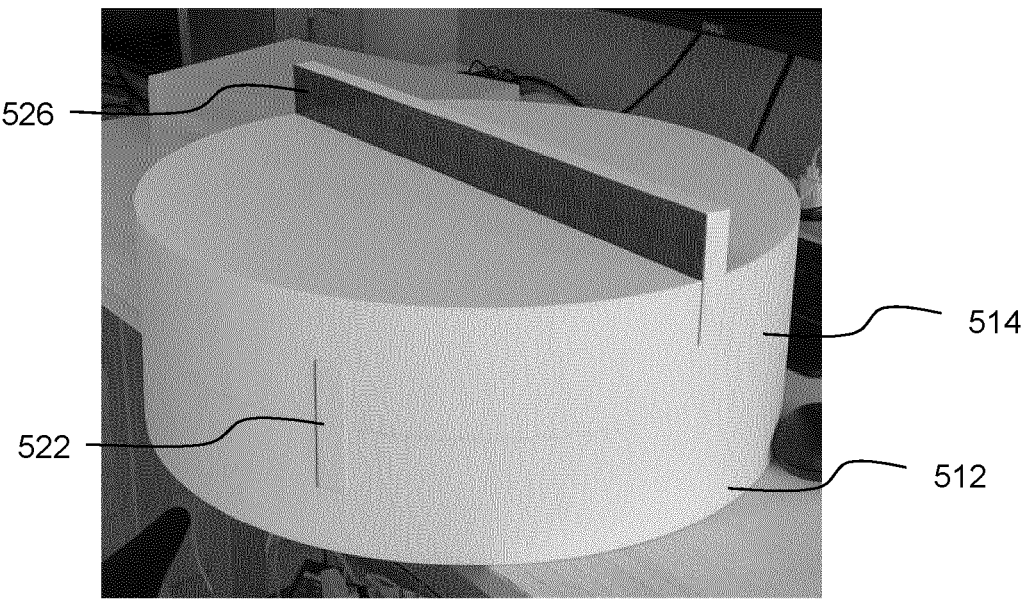
FIG. 5a depicts a partly disassembled phantom of FIGS. 4a and 4b, or else the phantom at an incomplete stage of manufacture.
Figure 5B:
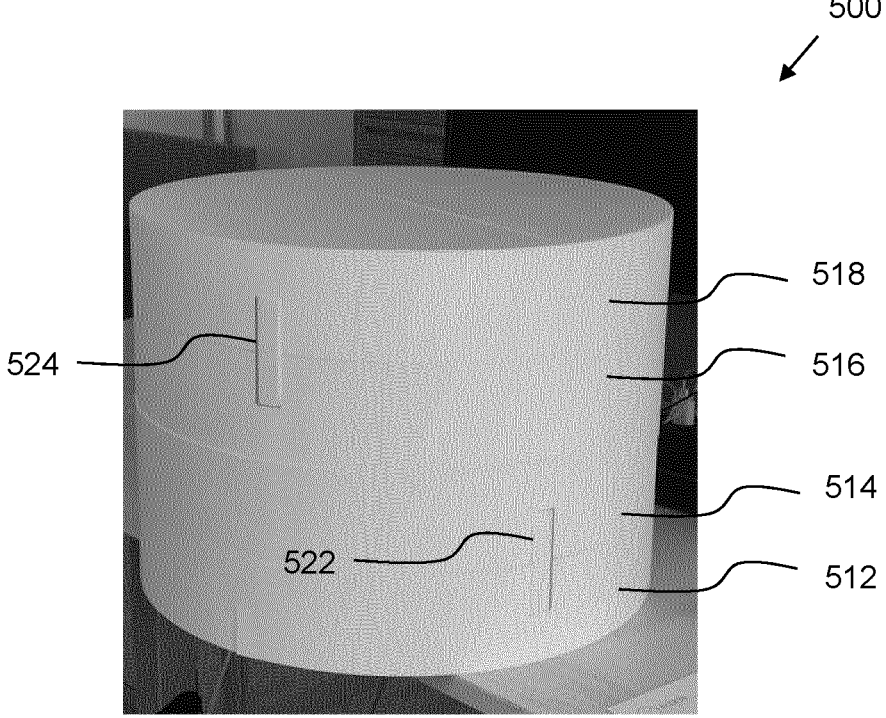
FIG. 5b depicts the phantom of FIGS. 4a and 4b.

FIGS. 5a and 5b depict a phantom 500 with a support structure comprised of stackable support elements 512, 514, 516, 518. The phantom 500 is in accordance with the phantom 400 described above with respect to FIGS. 4a and 4b. Each stackable element 512, 514, 516, 518 comprises at least one recess configured to receive a board 522, 524, 526. The stackable elements 512, 514, 516, 518 are configured to stack along the first (stacking) axis. The recesses run across the diameter of the support structure in a direction perpendicular to the stacking axis. The length of each recess is substantially equal to the length of each board 522, 524, 526. The depth of each recess, in a direction parallel to the stacking axis (or, equivalently, parallel to the length/central axis of the phantom) is substantially half the width of each board 522, 524, 526.

Each stackable support element 512, 514, 516, 518 comprises two opposing faces. For the phantom 500 depicted in FIGS. 5a, 5b, these opposing faces are circular. Two of the stackable support elements 512, 518 are end elements and are configured to be positioned at the ends of the completed stack of stacked support elements. These end support elements comprise a recess in which, in the assembled phantom 500, a board is positioned. This recess is formed in one of its faces. The remaining stackable support elements 514, 516 are internal stackable elements and comprise two recesses, each recess formed on one of the opposing circular faces of the internal stackable support element. The calibration phantom 500 can therefore be easily assembled from its component parts. During assembly of the phantom, a first board 522 is positioned in the recess of a first end stackable element 512. A first internal stackable support element 514 is stacked on top of the end stackable support element 512, with the board 522 positioned in one of the recess of the first internal stackable support element 514. The board 522 is therefore supported within the two recesses of the two stackable support elements 512, 514.

The recess on the opposing face of the first internal stackable support element 514 is now able to receive another board 514. The assembly depicted in FIG. 5*a* shows a phantom at this stage of assembly. The process of stacking the stackable support elements and positioning the boards such that they are held in place by the recesses of two different stackable support elements continues until the desired number of boards is reached, at which point the second end stackable element 518 completes the stack to form the assembled phantom 500.

FIGS. 5*a* 5*b* depict a phantom with a support structure which is comprised of a plurality of stackable elements 512, 514, 516, 518 each stacked along the stacking direction, each stackable element 512, 514, 516, 518 comprising at least one recess configured to hold one of the plurality of boards in position. The use of stackable support elements in this way is advantageous as it is a simple manufacturing method compared to the complex manufacturing methods required to produce prior phantoms such as the phantom depicted in FIG. 3. Also, the number of boards can be adjusted for different use cases (e.g. by adding more boards along the stacking axis to allow calibration of a helical scan where the object imaged is moved parallel to the rotation axis during the scan), or boards with different calibration patterns can be swapped in and out. This advantage cannot be provided by, for example, prior ball-bearing phantoms because for these phantoms the ball-bearing geometry is a known quantity which must be kept the same to provide ground truth information to the calibration methods. The use of recesses in stackable support elements is a simple and effective way of ensuring the boards remain flat and planar, as required for the calibration method.

FIG. 6 depicts an example calibration pattern for use with the presently disclosed phantoms. The pattern comprises a plurality of intersecting lines, which define points at their intersections. The calibration pattern comprises two sets of parallel lines. Each set of parallel lines extends in a direction which is non-parallel with both the length and the width axis of the board. The first set of parallel lines extends in a first direction, while the second set extends in a second, different direction. Where these lines intersect, an intersection point is defined. The intersecting lines define elongated diamonds, though the diamonds do not all have the same radiopacity. The radiopaque material is used to form diamonds of different radiopacity to form an alternating dark and light shading effect in projection images. There are two sets of diamonds: dark diamonds and light diamonds, where the dark diamonds have a higher degree of radiopacity in comparison with the light diamonds.

By forming a calibration pattern of two sets of intersecting lines, where both sets of lines extend in different directions, both directions being non-parallel with both the width and the length axis of the calibration pattern, lines of two different directions will be interrupted if a projection image does not capture the entire calibration pattern. This is depicted in FIG. 7*b*, which is an example of a projection image from a half fan scan. A projection of roughly half of the phantom is depicted. Interrupted lines 710 with two distinct directions of one of the calibration patterns extend off the edge of the projection image. In this way, opposing projection images from a half-fan scan are likely to capture a greater number of these interrupted lines. These opposing projection images will contain different parts of the same lines. By ensuring the same set of interrupted lines 710 are captured in different projection images in this way, calibration methods are able to provide a robust correspondence between opposing projections even when the same portion of the phantom is not visible in the two projections.

The pattern is a checkerboard pattern. Checkerboard patterns, or similar patterns of intersecting lines, are beneficially for finding 3D-2D correspondence, as the lines are accurately defined and provide many intersection points. This means there is a high accuracy in the determination of features in the phantom. Instead of squares, the pattern consists of elongated diamonds with their long axis parallel to the board length. The reason for using an elongated pattern is to facilitate pattern identification for boards imaged at narrow angles. The present calibration pattern comprises diamonds rather than rectangle or squares, and this provides several advantages. For example, a greater number of interrupted lines are formed in a half-fan scan, as demonstrated by numeral 710 in FIG. 7*b* and discussed above. Also, the projected lengths of the two line segments defining a corner section are evened out, with the hope of decreasing bias and the impact of noise in the edge identification. Also, the edge detection might be slightly biased, so that the detected edges are systematically shifted towards either the dark or bright region. This could for example be due to the algorithm, due to blurring of the projected edges or due to the etched copper edges not being perpendicular to the surface. One feature of the alternating dark and bright pattern is that lines identified in the image will most often consist of several boundaries of alternating direction, and thus the effect of any bias is reduced.

Figure 7A:
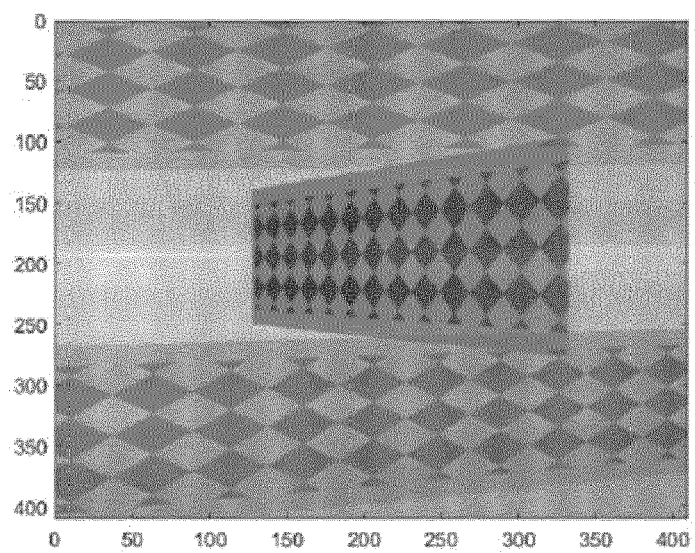
FIGS. 7a and 7b depict projection images of the phantom of FIGS. 4a and 4b, with different fields of view.
Figure 7B:
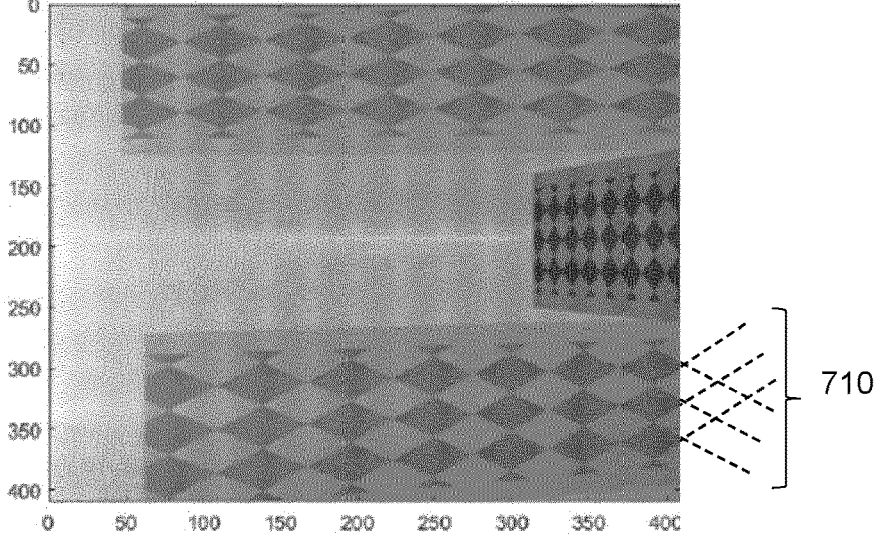

FIGS. 7*a*, 7*b* depict example phantom projections for small- and large-field-of-view imaging taken at the same projection angle. The x and y axes depict the position, in mm, on the detector. FIG. 7*a* is a smaller field of view image, taken by a CBCT imager in a full-fan configuration such as the one described above in respect of FIG. 2*a*. FIG. 7*b* is a larger field of view image, taken by a CBCT imager in a half-fan configuration such as the one described above in respect of FIG. 2*b*. The phantom in the projection images is a phantom in accordance with the phantom depicted in FIGS. 4*a*, 4*b*, 5*a*, 5*b*, comprising boards with the pattern depicted in FIG. 6.

Boards used in phantoms of the present disclosure may be manufactured using circuit board manufacturing techniques. Manufacturing techniques for electronic circuit boards, for example etching and lithography, are highly accurate processes where planar (2D) patterns can be made to an accuracy of micrometers. Further, the process is inexpensive. Copper, the material most commonly used in circuit boards, has the benefit of being radio-opaque. Patterns on circuit boards comprising copper will therefore be highly visible in x-ray imaging. The calibration patterns may be formed on PCB substrates using subtractive manufacturing methods such as chemical etching, physical milling, digital lithography, and/or photolithography.

Using an etching technique, highly attenuating copper patterns up to a couple of hundred micrometres in height and of lateral resolution down to a few tens of micrometres can be etched on backings of epoxy resin of almost arbitrary size.

The supporting structure of the phantom is, preferably but not essentially, a solid cylinder of low-density, rigid foam. This allows the boards to be supported along their entire lengths to avoid bending or warping and at the same time avoids sharp gradients in projected path lengths from different parts of the phantom. The support structure may be formed of a radiolucent material, such as a homogeneous foam. The material may be Styrofoam.

In an implementation in which the support structure surrounds and encases the boards, the support structure is formed of material which is more transparent to x-rays than the calibration patterns such that images of the form depicted in FIGS. 7a and 7b may be acquired. However, the support structure may take any of several different suitable forms.

Once projection images of the phantom are acquired from multiple gantry rotation angles, a processing step involves using an algorithm to determine the various geometric parameters, e.g. the position $(x_s, y_s, z_s)$ of the source of imaging radiation and the position $(x_d, y_d, z_d)$ and rotation $(xr_d, yr_d, zr_d)$ of the detector of the imaging scanner. These parameters, once determined, may be used to improve the accuracy when reconstructing future 3D images from projection images. The imaging scanner may then generate, and display, 3D tomographic images conditioned by the calibration parameters. These parameters may be referred to as calibration parameters herein, and each is indicative of a flex under gravity of the source of imaging radiation or detector.

The presently disclosed phantom comprises a plurality of boards, each having its own calibration pattern formed thereon. The six degrees of freedom (three translational and three rotational) of each additional pattern relative to a first pattern can be determined from the excess information provided by having two or more patterns in every projection image. Since each pattern defines a homography with eight degrees of freedom, in an example using two patterns, a single projection (in total $1 \times 2 \times 8 = 16$ equations) is enough to fully determine both the CBCT parameters and the relative orientation of the two boards ($1 \times 9 + 6 = 15$ degrees of freedom). However, more projections would improve the estimates of the relative pattern orientations (i.e. the phantom geometry) in the presence of noise.

The calibration algorithm locates edges in the projection images, fits lines to groups of edges and identifies these lines with the lines on the boards of the phantom. The line identification is based on a numerical model of the phantom which, given nine projection parameters and six relative position parameters for each board, outputs the expected positions of lines and intersections in the projection image. Once the lines in the projections have been identified, the coordinates of their intersection points are calculated. The optimal projection parameters and board positions are then obtained by solving an optimisation problem minimising distance between the intersection points and/or lines in the projections and their counterparts given by the numerical model.

At a high level, the calibration method comprises receiving projection images of the phantom taken from multiple gantry rotation angles and, based on the projection images, determining at least one calibration parameter indicative of a flex under gravity of the source of imaging radiation or detector.

Figures 9A, 9B:
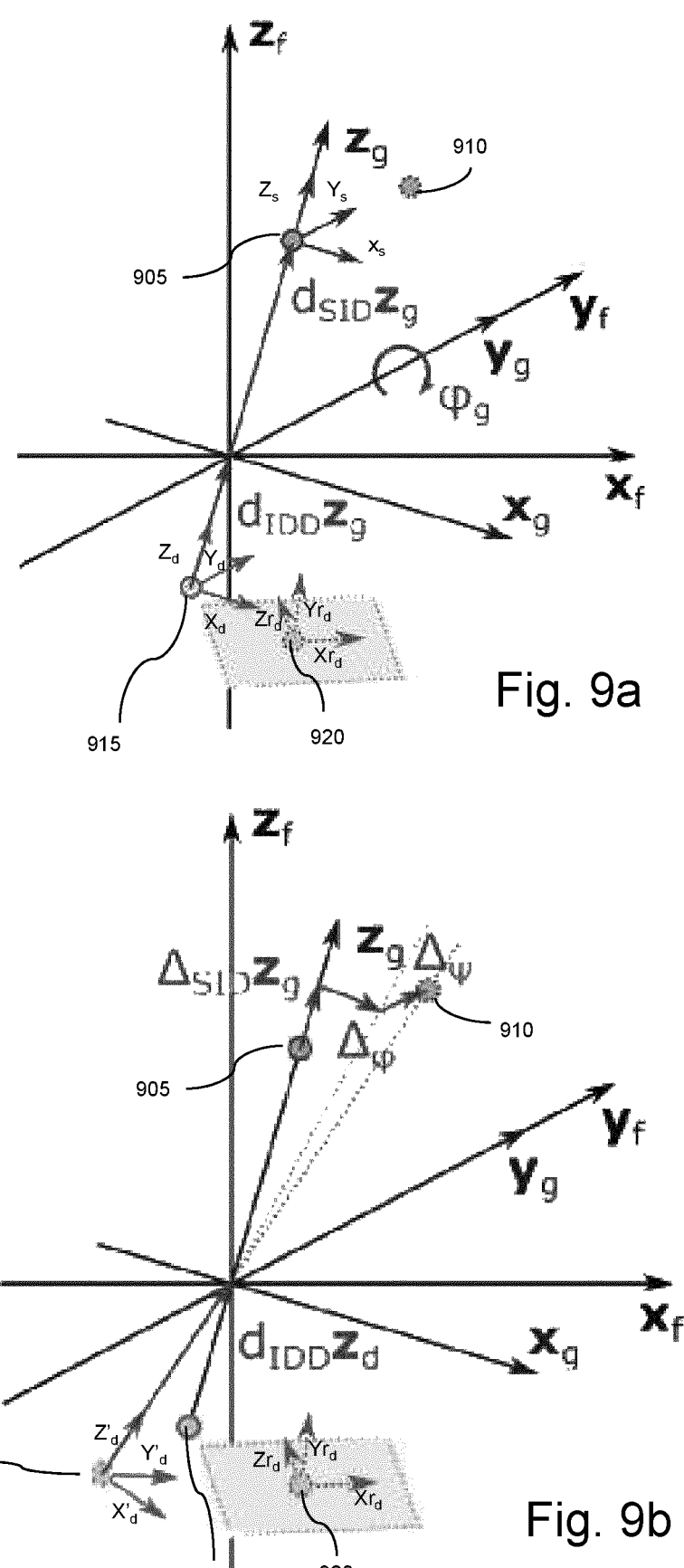
FIGS. 9a and 9b depict different mathematical co-ordinate systems which may be used in methods of the present disclosure.

The calibration parameters may be described in numerous different ways. FIGS. 9a and 9b depict example geometry parametrisations for an imaging scanner comprising a rotatable gantry, a source of radiation and a detector. FIG. 9a shows the positions and orientations of the local source and detector systems in the local-coordinate-system parametrisation. FIG. 9b illustrates the parameters of the true source position and shows the position and orientation of the local detector system in the source-coordinate-system parametrisation. Both sides include the fixed and gantry coordinate systems.

While the present method is described in relation to these coordinate systems and geometry parametrisations, the skilled person will understand that several choices in setting up these systems and parametrisations are either arbitrary, or have been selected to make the mathematics more efficient.

Accordingly, the particular coordinate systems and geometry parametrisations depicted in FIGS. 9a and 9b are set out herein merely to facilitate the understanding of the method and are not essential features of the present method.

FIGS. 9a and 9b depict different co-ordinate systems, in particular a fixed co-ordinate system $X_f$, $Y_f$, and $Z_f$ which is fixed with respect to the treatment room and a gantry co-ordinate system $X_g$, $Y_g$ and $Z_g$ which is fixed with respect to the nominal gantry rotation (and hence which is rotatable with respect to the fixed co-ordinate system). For an ideal gantry with perfectly circular detector and source trajectories, it is natural to let the origins of both these systems coincide with the imaging isocentre. However, as will be set out below, any fixed point in the room might be chosen as the origin with the only effect that the calibrated gantry parameters become translated and/or rotated. When performing the calibration, the isocentre is initially set to a point relative to the calibration phantom, for example a central diamond in a calibration pattern. Once these parameters are obtained, new parameters relative to an isocentre position which is independent of the phantom position in the gantry, can be defined and is often desirable.

In FIG. 9a is also depicted is a local source co-ordinate system $X_s$, $Y_s$, and $Z_s$ with an origin at a nominal source position 905 found at the nominal source-isocentre distance (SID) from the isocentre along the positive $Z_g$-axis and with its axes parallel to the gantry co-ordinate system; and a local detector co-ordinate system $X_d$, $Y_d$, and $Z_d$ with an origin at a nominal detector position 915 found at the nominal isocentre-detector distance (IDD) along the negative $Z_g$-axis and its axes parallel to the gantry co-ordinate system.

FIG. 9a depicts, for a particular gantry rotation angle $\phi_g$, a nominal source position 905, i.e. the position that the source of radiation would have in a mathematically ideal system, and the true source position 910, i.e. the actual position of the source. The true source position 910 and the nominal source position 905 differ from one another in part, or entirely, due to sagging/flexing effects caused by gravity. The true source position 910 can be described using the local source co-ordinate system, with co-ordinates $X_s$, $Y_s$, $Z_s$. The nominal piercing point position 915 is the point on the detector onto which the isocentre is projected in the nominal geometry, i.e. the point on the detector onto which the isocentre is projected from the nominal source position 905. The nominal piercing point position 915 can be used as the origin for the local detector co-ordinate system with co-ordinates $X_d$, $Y_d$, $Z_d$, as described above.

FIG. 9b, depicts an alternative parametrisation of the projection geometry. Here, the expected position 925 of the nominal piercing point is the point located at the nominal IDD from the isocentre along the direction given by the vector from the true source position 910 to the isocentre. This expected position 925 of the nominal piercing point can be used as the origin for another local detector co-ordinate system $X'_d$, $Y'_d$, $Z'_d$, with axis, $Z'_d$ parallel to the vector from the osicentre to the true source position and axis $X'_d$ in the XZ-plane of the fixed coordinate system. In this parametrisation, the true source position is given by ASID (describing the distance between the nominal source position 905 and the true source position 910 along the $Z_g$ axis), $\Delta\phi$ (the in-plane angular difference between the nominal source position 905 and the true source position 910) and Au (the out-of-plane angular difference between the nominal source position 905 and the true source position 910).

The true position 910 of the source can be described either in the fixed system, in the gantry system, its the local coordinate system or by parameters ASID, $\Delta\phi$ and $\Delta\psi$.

17

Similarly, the true position 920 of the nominal piercing point can be described in the fixed system, the gantry system or in either of the local detector co-ordinate systems in FIGS. 9a and 9b. Finally, the true orientation of the detector must be taken into account. The true detector orientation can be described by three rotation parameters $X_{rd}$, $Y_{rd}$, and $Z_{rd}$, which can be expressed in any of the aforementioned co-ordinate systems. As set out above, different parameterisations may be used according to the present methods.

Algorithm 1 gives a detailed overview of one implementation of a suitable algorithm suitable for determining calibration parameters based on the calibration phantom depicted in FIGS. 4a and 4b.

Algorithm 1

Input:

set of N projection images P model M mapping 9 projection parameters $\alpha_i$ and 18 board parameters $\beta$ to a set $$L_i^*$$

of projected lines (and their intersection points $$X_i^*)$$

9N nominal projection parameters $\alpha^{nom}$ and 18 nominal board parameters $\beta^{nom}$ Output:

9N optimised projection parameters $\alpha^{opt}$ and 18 optimised board parameters $\beta^{opt}$ For each of the N projection images:

$E_i$←find set of edge coordinates in projection image $P_i$ $$L_i^{nom} \leftarrow$$

create smoothed dark image of expected set of lines $$L_i^{nom} = M(\alpha_i^{nom}, \beta^{nom})$$

in projection $P_i$ t←find rigid 2D translation of $$L_i^{nom}$$

minimising its values at $E_i$ $$L_i \leftarrow L_i^{nom} + t$$

project edges in $E_i$ onto the lines of $L_i$ $G(E_i, L_i)$←associate each edge in $E_i$ with all lines in $L_i$ within distance and direction thresholds find the 18 board parameters $\beta^+$ that minimise the shortest distances between each edge in $E_i$ and any associated line in

18

$$L_i^{nom} = M(\alpha_i^{nom}, \beta)$$

according to $G(E_i, L_i)$ $L_i$←based on the previous step, create updated set of expected line segments $$M(\alpha_i^{nom}, \beta^+)$$

project edges in $E_i$ onto the lines of $L_i$ $F(E_i, L_i)$←map each edge in $E_i$ to its closest line in $L_i$ if within distance and normal thresholds $L_i$←for each line in $L_i$, select a fraction of its closest edges in $F(E_i, L_i)$ and fit a new line $F^*(E_i, L_i)$←map each edge in $E_i$ to its closest line in $L_i$ if within distance and normal thresholds $L_i$←for each line in $L_i$, fit a line to all its edges in $F^*(E_i, L_i)$ $X_i$←find the set of intersections points between all lines of $L_i$ $\alpha^{opt}$, $\beta^{opt}$←find the 9N+18 calibration parameters by minimising, simultaneously for all projection angles i, the 2D distances between points in $X_i$ and modelled points $$X_i^* = M(\alpha_i, \beta)$$

FIG. 8 depicts a calibration method 800. Such a method is suitable for calibrating an imaging scanner comprising a rotatable gantry. A system for calibrating such a 3D scanner may comprise the 3D scanner, a phantom as described elsewhere herein, and a computer-readable medium comprising computer-executable instructions which, when executed by a processor, cause the processor to perform the method depicted in FIG. 8.

At block 801, a plurality of projection images taken from multiple gantry rotation angles is received at the processor. This block may further comprise acquiring the images, for example sending instructions to the imaging scanner to perform a scan to obtain the images. The projection images each depict a phantom placed in the field of view of the imaging scanner. The phantom comprises a plurality of calibration patterns in the manner described above. In use, the phantom is positioned in the imaging scanner with its first axis substantially parallel with the gantry rotation axis. The received images may be of the form of those depicted in FIGS. 7a and 7b.

At block 802, the positions of edge points in the projection images are located for each projection image. Edge points may be described as features of the image. Depending on the algorithm used, edge points may occur at points in the image at which the brightness changes sharply, or points at which the projection image displays some other discontinuity. These edge points are likely to occur at the boundaries of objects and at the boundaries of regions of differing radiopacity. Therefore, at least some of the edge points detected at block 802 are likely to be associated with the calibration patterns of the phantom, some edge points are likely to be associated with the boundaries of the support structure, and some may not be associated with the phantom at all but instead be associated with 'background' such as the structure of the patient positioning surface on which the phantom is placed. Edge detection algorithms are known to the skilled person, such as the Sobel edge detector. An advantage of the Sobel edge detector is its simplicity, making it easy to implement and fast to run.

At block 803, each identified edge point position is associated with, at most, one of the lines of the calibration pattern. The method therefore comprises associating each identified edge point position with at most one of the lines defined by the intersecting lines in the calibration patterns; for example, the lines defined by the diamond shapes in the calibration pattern of FIG. 6. Not all edges in the image need be associated with a line of the calibration pattern because, for example, some of the edges identified at block 802 may be associated with the boundaries of the boards or with discontinuities in the support structure. Block 803 involves using the known calibration pattern, and may comprise assigning identified edge points to possible or trial lines of the known pattern, and iteratively updating the assignments of identified edge points to the lines of the known calibration pattern as more edge point position are identified and assigned. The process at this block can be achieved using known algorithms.

In a specific implementation, the step of associating identified edge points with lines from the calibration pattern in each projection image may be a multi-step procedure. In such an implementation, in each step, a line pattern guess is improved and, based on the improved line pattern guess, edge points in the projection image are associated to lines in the known calibration pattern. In such a multi-step procedure, first, the image of the expected line pattern on the detector, given a nominal gantry geometry (i.e. a gantry geometry according to a mathematically ideal system in which there is no flexing or sagging), gantry angle and phantom geometry, is calculated and optionally blurred. Then, the rigid shift of this image which minimises the distance between the pattern and the detected edge points is approximated by minimising the square of the sum of the values of the (optionally blurred) image at the edge point positions. Next, the edge points are projected onto the translated line segments of the expected projected line pattern. An edge point is tentatively associated with a line segment where the distance is below a given threshold and the edge normal is close enough to the normal of the projected line. These associations may be described as 'trial' associations. Identified edges not associated with any line of the calibration pattern after this initial step do not participate in the next step.

Following this, the position and translation of each board which minimises the sum of the squared distances from each participating edge point to its associated projected line is found. The resulting expected line pattern becomes a guess for the true line pattern. Note that this step serves to find a good guess for the true line pattern and therefore the board orientations which are calculated here differ for each gantry angle and may not be used in subsequent steps. All edge points are, once more, projected onto the improved guess of the line pattern. This time, an edge point is only associated to its closest projected line, provided these are close enough and have gradients parallel enough. In this step, the minimum distance threshold is lowered compared to in the previous step.

At block 804, for each projection image, lines are fitted to all edge points associated with the same line in the calibration pattern. This stage comprises fitting line segments to a fraction of the closest edge points associated with each line on the calibration pattern, provided the line has enough edge points associated with it. These segments constitute a final estimate for the projected line pattern. Each edge point which is close enough to its closest line segment in the estimate becomes permanently associated with the corresponding line in the calibration pattern. The best line fits for the edges associated with each line are obtained.

At block 805, the intersection points of the fitted lines are identified. These intersection points are now expected to correspond to the corner positions of the projected diamond shapes. Together, blocks 804 and 805 comprise fitting a line in the projection image(s) to all points associated with the same line in the calibration pattern(s) and calculating the intersection points between fitted lines in the image. Each intersection point corresponds uniquely to a corner in the checkerboard pattern. Steps 802 to 805 take, on average, a couple of seconds to complete for a 1024×1024-pixel projection image.

At block 806, at least one parameter indicative of a flex under gravity is determined. This determination is based on the processing performed at blocks 802-805, and in particular is based on the identified intersection points of the fitted lines. The determined parameter is indicative of the flex under gravity of either the source of imaging radiation or the detector, e.g. one of the following: the position $(x_d, y_d, z_d)$ of the source of imaging radiation and the position $(x_d, y_d, z_d)$ and rotation $(xr_d, yr_d, zr_d)$ of the detector of the imaging scanner. In a preferred approach, these nine projection/ calibration parameters are found simultaneously for each projection angle, and, in addition, the six relative position parameters for two of the boards are found too, by minimising the sum of the squared distances between corner points in the image and the pattern projected by the model.

In an example, at block 806, the calibration parameter values may be obtained through nonlinear optimisation of the sum of the squared 2D distances between the identified intersection points and the corresponding points predicted by the numerical model. This is done for example by iteratively changing the projection parameter(s) and the parameters describing the pattern board positions in a systematic way, for example by using the Levenberg-Marquardt algorithm. The result is the six orientation parameters each for two of the pattern boards and nine projection (calibration) parameters for each gantry angle represented by the projection images received at block 801. Accordingly, each of the nine calibration parameters is determined as a function of gantry angle.

In summary then, the optimisation process feeds parameters (projection parameters and those describing the relative positions of the phantom boards) to a numerical model, uses the numerical model to predict the positions of intersection points, calculates the distance between the expected intersection points and the identified intersection points and then iterates until this distance between the expected intersection points based on the parameters and the detected locations of the intersection points is small, e.g. below a threshold.

When using a phantom which comprises three boards, such as the phantom 400 depicted in FIGS. 4a and 4b, the centre point of the middle calibration pattern is a suitable point to be defined as the origin of the fixed coordinate system, and the long edge, short edge and normal direction of this board define the x, y, and z-axes of this coordinate system, respectively. Of course, the calibration method can be designed to use a different point to define an origin of a fixed coordinate system, though the central diamond of the central checkerboard is particularly useful because, in an ideal setup and with ideal phantom placement, it will coincide with the isocentre of the CBCT scanner and radiotherapy machine.

The calibration result is contained in a CBCT geometry object which holds three different parametrisations of the same geometry. The fixed-coordinate-system parametrisation gives the absolute (or 'true') source and detector coordinates and the detector rotation angles relative to the fixed system defined by the phantom. For example, the true source position 910 for each gantry angle is expressed in in its coordinates along the $X_f$, $Y_f$, and $Z_f$ axes. The local-coordinate-system parametrisation gives the deviations compared to their nominal values for source position, detector position and detector rotation, expressed in their respective local coordinate systems shown in FIG. 9a. Similarly, the source-coordinate-system parametrisation uses ASID, $\Delta\phi$ and $\Delta\psi$ describe the true source position and expresses the detector position and rotation in the local system shown in FIG. 9b. As set out above with respect to FIGS. 9a and 9b, these local coordinate systems are the coordinate systems with origins at the expected source/piercing point positions, given the nominal SID/IDD and reported gantry angle $\phi$, rotated so that their coordinate axes are parallel to those of the gantry coordinate system. In the source-coordinate-system parametrisation, the source position is parametrised by the deviations compared to the nominal geometry in SID, in in-plane angle (i.e. gantry angle $\phi$) and out-of-plane angle $\psi$ with respect to the phantom-defined origin/isocentre. The origin of the local detector coordinate system in this parametrisation is then taken to be the point at distance IDD from the isocentre (or an origin point defined by the phantom) along the direction from the true source position to the isocentre. The local detector coordinate system is oriented such that the z-axis is parallel to the vector from the isocentre to the source and the x-axis parallel to the xz-plane of the fixed coordinate system. The detector parameters are then defined as deviations from the nominal position and rotation in this system.

Defining the centre point of the phantom to be the fixed coordinate system origin is somewhat arbitrary and makes the obtained parameter values dependent on the orientation of the phantom in the gantry. Although this does not affect image reconstruction, it is undesirable when comparing calibrations made at different time points or matching coordinate systems. It is possible to instead express the calibration in a coordinate system that is independent of phantom orientation. A possible choice is to find a coordinate system where the deviations in projection parameters are, in some sense, as small as possible from their nominal values. However, it can never be guaranteed that the origin of such a system does not move in relation to the room coordinates for two subsequent calibrations with different source and detector trajectories. Therefore, even for reproducible flex, the calculated origin might differ between different detector positions or gantry rotation directions. To have a common origin between different calibrations and the MV-system, the calibrated coordinates must therefore be related to a fixed reference, for example on the table.

In a particular implementation, the "best-fit" fixed coordinate system is obtained in a separate step after calibration. First, the average radii and the coordinates of the source and detector trajectories in their respective centre-of-mass systems are calculated. The average rotation axis is then determined as the normal of the plane fitted to the union of these source and detector positions, scaled so their mean radii are the same. This axis defines the y-axis direction in the new fixed system. For each gantry angle, the expected centre point is given by taking the vector pointing from the source to the detector, dividing it by the average magnification (given by the source and detector radii) and adding it to the source position. The isocentre of the new fixed system is then found by calculating the average centre point and finding the intersection between on the one hand the source trajectory plane, and on the other a line defined by the average centre point and the y-axis direction. The remaining rotational degree of freedom of the new system is finally determined by minimising the difference between the reported gantry angle and the angle of the source position. This new fixed coordinate system obtained is unaffected by global rotations and translations of the initial fixed system, and thus of the phantom. Once the parameters in best-fit fixed coordinate system is obtained, the parameters in the corresponding local and source systems are calculated.

While the discussion in the present application is focused on a CBCT imaging scanner that forms part of a radiotherapy device, it should be appreciated that the phantom and calibration methods disclosed herein are equally applicable for calibrating other x-ray flat panel systems such as tomosynthesis and stereoscopic pair imaging.

Due to the almost translation invariant nature of the projected calibration patterns for some gantry angles, correct association of edges to lines is sensitive to the phantom position starting estimate. Therefore, in some implementations of the present phantom, the calibration patterns on each board comprise a mark, e.g. a circle, on the central diamond in each pattern (not shown in the figures). Such markers would be easily detectable in the projections and from those an improved starting estimate for the phantom position could be obtained. If very large detector shifts are desirable, e.g. to effect large differences in field of view, a mark on the diamonds at a fixed distance on either side of the middle one can be used to further improve the accuracy of the starting position estimate. Another method for improving the starting position estimate is to look for projections where one of the boards is imaged close to edge on. The projection of the board then becomes a dark line from which the phantom rotation, and translation, can be estimated.

Algorithm 1 and the calibration method described above in relation to FIG. 8 describe making use of edge detection algorithms, assigning the identified edges to lines of the calibration pattern, fitting lines to all points assigned to the same lines, identifying intersection points, and determining calibration parameters based on the identified intersection points and knowledge of the expected calibration pattern. However, other calibration algorithms and techniques may be used. For example, image registration and/or pattern fitting techniques may be used to find the best fit between each projection image and the expected projected pattern based on existing knowledge of the calibration pattern. By assessing the image transformations required, it is possible to determine the calibration parameters.

The methods described herein are suitable for finding calibration parameters which describe the difference between a nominal and a true position for a source of radiation, and the difference between a nominal and a true position and orientation for a detector. The difference between the nominal and true positions/orientations are primarily caused by flexing of the heavy components under gravity and accordingly the calibration parameters are indicative of a flex under gravity. However, it should be appreciated that the calibration parameters may be further indicative of other potential sources of discrepancy between nominal and true positions/orientations. Other sources of discrepancies between nominal and true values of the source and detector parameters include: manufacturing tolerances, gantry wobble (rotation of the gantry not in-plane), various mechanical misalignments, discrepancies between reported and actual gantry position due to hysteresis effects, changing engine load or acceleration, and vibrations.

The phantom 400 depicted in FIGS. 4a 4b comprises a plurality of boards which are positioned along a first axis. The first axis 430 here is a line which passes through each board. However, the first axis need not be an axis which passes through each board, but rather the first axis merely defines a direction along which the boards are positioned with respect to one another. The first axis can be thought of as an axis of a co-ordinate system which can be used to define the relative position of each board, and the boards are positioned, e.g. separated or spaced, along this axis. For example, the centres of each board would have a different co-ordinate value in a co-ordinate system using the first axis. It is not necessary that a single axis, or line, can be drawn which would contact each board, as is the case in the accompanying figures. Similarly, though the first axis 430 depicted in FIG. 4b aligns with the central axis of the cylindrical support structure 410, this need not be the case. The support structure may have take numerous shapes and may not have a central axis. Accordingly, it should be understood that the first axis is an axis which can be defined in space, and is not necessarily defined by the symmetrical nature of the support structure.

Figure 11:
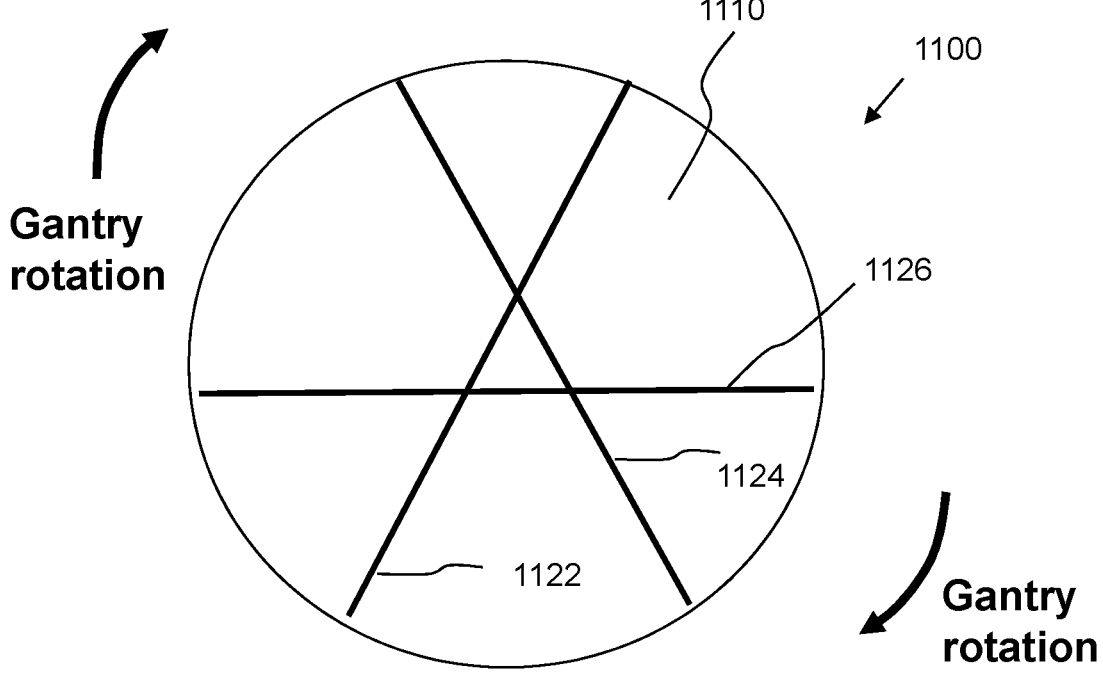
FIG. 11 is another implementation of a phantom according to the present disclosure.

To illustrate this point, an alternative implementation of a phantom according to the present disclosure is depicted in FIG. 11. FIG. 11 is similar in many respects to the phantom 400 depicted in FIG. 4, and FIG. 11 similarly shows a view from the base (or equivalently from the top) of the phantom. The support structure 1110 of the phantom is depicted as transparent except for its outline to aid understanding regarding the arrangement of the boards 1122, 1124, and 1126. As with phantom 44, phantom 1100 comprises a support structure 1110 and a plurality of boards 1122, 1124, 1126. Each board 1122, 1124, 1126, comprises a planar calibration pattern formed of radiopaque material. The boards are positioned, by the support structure, in an arrangement along a first axis. The first axis is into the plane of the page of FIG. 11 and aligns with the central axis of the support structure 1110. However, crucially, the first axis does not pass through any of boards 1122, 1124, 1126.

As with phantom 400, each board 1122, 1124, 1126 is positioned, by the support structure 1110, at an angle with respect to each of the other boards 1122, 1124, 1126 such that each planar calibration pattern faces a different direction. The directions faced by each planar calibration pattern are substantially perpendicular to the first axis.

As discussed above, the presently disclosed phantom(s) and associated calibration method(s) are advantageous over known approaches. By providing a calibration phantom in which boards comprising calibration patterns are positioned, by a support structure, at an angle to each of the other boards such that each planar calibration pattern faces a different direction, wherein the directions faced by each planar calibration pattern are substantially perpendicular to the first axis along which the boards are stacked, it is ensured that at least a portion of a calibration pattern is visible in every projection image when the calibration phantom is imaged. In an arrangement comprising three or more boards, with each board positioned at an oblique angle to the other boards, it can be assured that at least a portion of the calibration patterns of two different boards are visible in every projection image.

Because the disclosed calibration method is capable of determining the relative positions of the boards in the phantom, the only manufacturing accuracy needed is in relation to the calibration patterns. Such patterns can be formed on boards using circuit board manufacturing techniques, which are both highly accurate and inexpensive.

Figure 10:
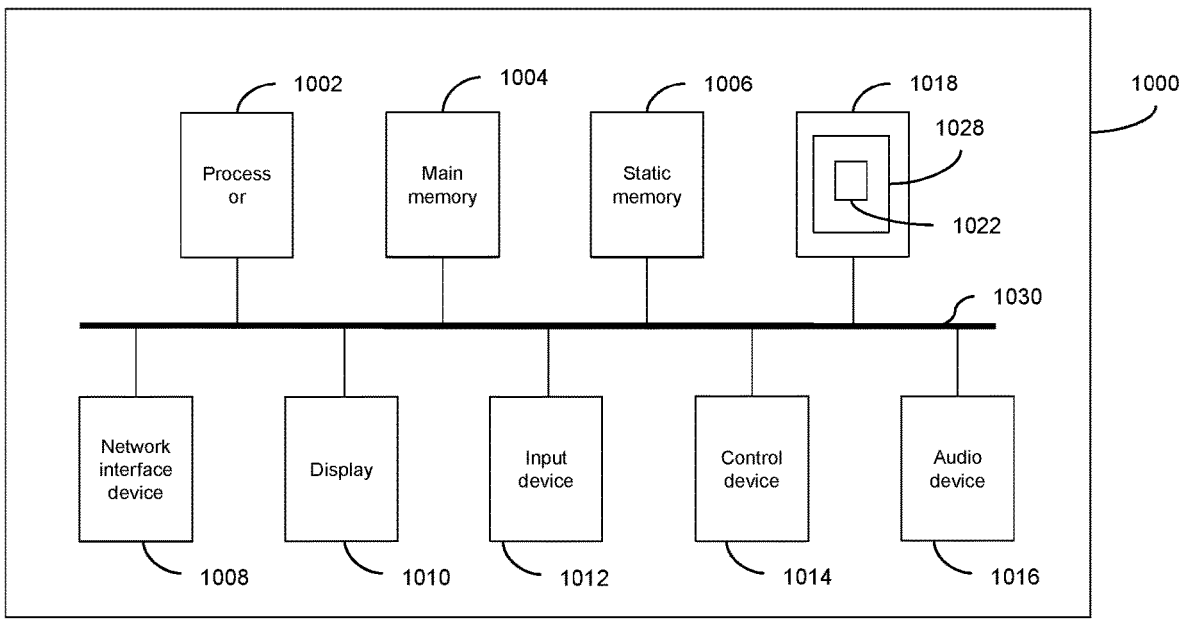
FIG. 10 is a block diagram depicting an implementation of a computing device configured to carry out methods of the present disclosure.

FIG. 10 illustrates a block diagram of one implementation of a computing device 1000 within which a set of instructions for causing the computing device to perform any one or more of the methodologies discussed herein, may be executed. The computing device may form part of a radiotherapy device. In implementations, the computing device may be connected (e.g., networked) to other machines in a Local Area Network (LAN), an intranet, an extranet, or the Internet. The computing device may operate in the capacity of a server or a client machine in a client-server network environment, or as a peer machine in a peer-to-peer (or distributed) network environment. The computing device may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single computing device is illustrated, the term "computing device" shall also be taken to include any collection of machines (e.g., computers) that individually or jointly execute a set (or multiple sets) of instructions to perform any one or more of the methodologies discussed herein.

The example computing device 1000 includes a processing device 1002, a main memory 1004 (e.g., read-only memory (ROM), flash memory, dynamic random access memory (DRAM) such as synchronous DRAM (SDRAM) or Rambus DRAM (RDRAM), etc.), a static memory 1006 (e.g., flash memory, static random access memory (SRAM), etc.), and a secondary memory (e.g., a data storage device 1018), which communicate with each other via a bus 1030.

Processing device 1002 represents one or more general-purpose processors such as a microprocessor, central processing unit, or the like. More particularly, the processing device 1002 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 1002 may also be one or more special-purpose processing devices such as an application specific integrated circuit (ASIC), a field programmable gate array (FPGA), a digital signal processor (DSP), network processor, or the like. Processing device 1002 is configured to execute the processing logic (instructions 1022) for performing the operations and steps discussed herein.

The computing device 1000 may further include a network interface device 1008. The computing device 1000 also may include a video display unit 1010 (e.g., a liquid crystal display (LCD) or a cathode ray tube (CRT)), an alphanumeric input device 1012 (e.g., a keyboard or touchscreen), a cursor control device 1014 (e.g., a mouse or touchscreen), and an audio device 1016 (e.g., a speaker).

The data storage device 1018 may include one or more machine-readable storage media (or more specifically one or more non-transitory computer-readable storage media) 1028 on which is stored one or more sets of instructions 1022 embodying any one or more of the methodologies or functions described herein. The instructions 1022 may also reside, completely or at least partially, within the main memory 1004 and/or within the processing device 1002 during execution thereof by the computer system 1000, the main memory 1004 and the processing device 1002 also constituting computer-readable storage media.

The various methods described above may be implemented by a computer program. The computer program may include computer code arranged to instruct a computer to perform the functions of one or more of the various methods described above. The computer program and/or the code for performing such methods may be provided to an apparatus, such as a computer, on one or more computer readable media or, more generally, a computer program product. The computer readable media may be transitory or non-transitory. The one or more computer readable media could be, for example, an electronic, magnetic, optical, electromagnetic, infrared, or semiconductor system, or a propagation medium for data transmission, for example for downloading the code over the Internet. Alternatively, the one or more computer readable media could take the form of one or more physical computer readable media such as semiconductor or solid state memory, magnetic tape, a removable computer diskette, a random access memory (RAM), a read-only memory (ROM), a rigid magnetic disc, and an optical disk, such as a CD-ROM, CD-R/W or DVD.

In an implementation, the modules, components and other features described herein can be implemented as discrete components or integrated in the functionality of hardware components such as ASICS, FPGAS, DSPs or similar devices.

A "hardware component" is a tangible (e.g., non-transitory) physical component (e.g., a set of one or more processors) capable of performing certain operations and may be configured or arranged in a certain physical manner. A hardware component may include dedicated circuitry or logic that is permanently configured to perform certain operations. A hardware component may be or include a special-purpose processor, such as a field programmable gate array (FPGA) or an ASIC. A hardware component may also include programmable logic or circuitry that is temporarily configured by software to perform certain operations.

Accordingly, the phrase "hardware component" should be understood to encompass a tangible entity that may be physically constructed, permanently configured (e.g., hardwired), or temporarily configured (e.g., programmed) to operate in a certain manner or to perform certain operations described herein.

In addition, the modules and components can be implemented as firmware or functional circuitry within hardware devices. Further, the modules and components can be implemented in any combination of hardware devices and software components, or only in software (e.g., code stored or otherwise embodied in a machine-readable medium or in a transmission medium).

Unless specifically stated otherwise, as apparent from the following discussion, it is appreciated that throughout the description, discussions utilizing terms such as "receiving", "determining", "locating", "associating", "identifying," or the like, refer to the actions and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

It is to be understood that the above description is intended to be illustrative, and not restrictive. Many other implementations will be apparent to those of skill in the art upon reading and understanding the above description. Although the present disclosure has been described with reference to specific example implementations, it will be recognized that the disclosure is not limited to the implementations described, but can be practiced with modification and alteration within the spirit and scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

The invention claimed is:

1. A calibration phantom for calibrating an imaging scanner, the imaging scanner comprising a rotatable gantry, and a source of imaging radiation and a detector both configured to rotate with the rotatable gantry, the calibration phantom comprising:

a support structure and a plurality of boards, wherein each board comprises a planar calibration pattern formed of radiopaque material, wherein the plurality of boards are positioned along a linear first axis, wherein each board of the plurality of boards is positioned, by the support structure, at an angle with respect to each of the other boards in the plurality of boards such that each planar calibration pattern faces a different direction, wherein the directions faced by each planar calibration pattern are substantially perpendicular to the linear first axis, wherein each board of the plurality of boards has a center, and wherein each board of the plurality of boards are positioned such that the centers are spaced apart from each other in a direction of or parallel with the linear first axis.

2. The calibration phantom of claim 1, where the plurality of boards comprises at least three boards, wherein each board of the plurality of boards is positioned, by the support structure, at an oblique angle with respect to the other boards such that each planar calibration pattern faces a different direction.

3. The calibration phantom of claim 2, wherein each board in the plurality of boards is positioned, by the support structure, such that when the calibration phantom is imaged via imaging radiation incident from any direction perpendicular to the first axis, at least a portion of at least two planar calibration patterns are included in the image.

4. The calibration phantom of claim 1, wherein the plurality of boards comprises at least a first board comprising a first planar calibration pattern, a second board comprising a second planar pattern, and a third board comprising a third planar pattern, wherein the first planar pattern is positioned, by the support structure, to face in a first direction, wherein the second planar pattern is positioned, by the support structure, to face in a second direction, and the third planar pattern is positioned, by the support structure, to face in a third direction, and wherein the first direction, the second direction, and the third direction all meet at oblique angles with respect to one another.

5. The calibration phantom of claim 1, wherein each board of the plurality of boards are separated from one another along the first axis.

6. The calibration phantom of claim 1, wherein each board of the plurality of boards comprises a substrate, and wherein the planar calibration pattern is formed of metal layered on the substrate.

7. The calibration phantom of claim 6, wherein each of the planar calibration patterns is formed via a subtractive manufacturing process, and wherein the subtractive manufacturing process comprises one or more of the following processes:

chemical etching, physical milling, digital lithography, photolithography.

8. The calibration phantom of claim 1, wherein the support structure has a central axis aligned with or parallel to the first axis.

9. The calibration phantom of claim 1, wherein the support structure is comprised of a plurality of stackable elements each stacked along the first axis, each stackable element comprising at least one recess configured to hold one of the plurality of boards in position.

10. The calibration phantom of claim 1, wherein the planar calibration patterns each comprise a plurality of intersecting lines.

11. The calibration phantom of claim 10, wherein the planar calibration patterns are checkerboard patterns comprising a repeating pattern of diamonds.

12. A method of calibrating an imaging scanner, the imaging scanner comprising a rotatable gantry, and one or more components configured to rotate with the gantry, the one or more components comprising a source of imaging radiation and a detector, the method comprising:

receiving a plurality of projection images of a phantom positioned within a field of view of the imaging scanner, wherein the projection images are taken from multiple gantry rotation angles, and wherein the phantom comprises a plurality of boards each comprising a calibration pattern formed of radiopaque material, and wherein each board of the plurality of boards is positioned, by a support structure, at an oblique angle to each of the other boards in the plurality of boards such that each planar calibration pattern faces a different direction; and determining, based on the projection images, at least one calibration parameter, wherein the at least one calibration parameter is indicative of a difference between a nominal position or orientation of a component of the imaging scanner compared to a true position or orientation of the component of the imaging scanner.

13. The method of claim 12, wherein the difference between the nominal position or orientation of the component and the true position or orientation of the component is indicative of flexing under gravity of the component.

14. The method of claim 12, wherein the method further comprises:

identifying a position of one or more edge points in each projection image; and associating the identified edge point positions with lines of the calibration pattern.

15. The method of claim 12, wherein the calibration pattern further comprises a plurality of intersecting lines, where the lines intersect to form intersection points, and the method further comprises:

identifying the intersection points in the projection images; and determining the at least one calibration parameter based on the identified intersection points in each projection image.

16. The method of claim 12, wherein the at least one calibration parameter relates to at least one of a position of the source of imaging radiation, a position of the detector, and an orientation of the detector.

17. The method of claim 12, wherein the at least one calibration parameter is determined as a function of at least one gantry rotation angle of the multiple gantry rotation angles.

18. A non-transitory computer-readable medium comprising computer-executable instructions which, when executed by a processor, cause the processor to:

receive one or more projection images of a phantom positioned within a field of view of an imaging scanner, wherein the one or more projection images are taken from multiple gantry rotation angles, wherein the phantom includes a plurality of boards, wherein each board of the plurality of boards includes a calibration pattern formed of a radiopaque material, wherein each board of the plurality of boards is positioned, by a support structure, at an oblique angle to each of the other boards in the plurality of boards such that each planar calibration pattern faces a different direction; and determine, based on the one or more projection images, at least one calibration parameter, wherein the at least one calibration parameter is indicative of a difference between a nominal position or nominal orientation of a component the imaging scanner compared to a true position or a true orientation of the component of the imaging scanner.

19. A system for calibrating an imaging scanner, the imaging scanner comprising a rotatable gantry, and components configured to rotate with the gantry, the components comprising a source of imaging radiation and a detector, the system comprising:

a phantom comprising a plurality of boards, each board of the plurality of boards comprising a calibration pattern formed of radiopaque material, and each board of the plurality of boards being positioned, by a support structure, at an oblique angle to each of the other boards in the plurality of boards such that each planar calibration pattern faces a different direction; and a computer-readable medium comprising computer-executable instructions which, when executed by a processor, cause the processor to:

receive multiple projection images of the phantom taken by the imaging scanner from multiple gantry rotation angles; and determine at least one calibration parameter based on the multiple projection images, wherein the at least one calibration parameter is indicative of a difference between a nominal position or a nominal orientation of a component of the imaging scanner compared to a true position or a true orientation of the component of the imaging scanner.

20. The non-transitory computer-readable medium of claim 18, wherein the imaging scanner includes a rotatable gantry and one or more components configured to rotate with the rotatable gantry, wherein the one or more components includes a source of imaging radiation or a detector.

* * * * *